US010806144B2

(12) United States Patent
Modak et al.

(10) Patent No.: US 10,806,144 B2
(45) Date of Patent: Oct. 20, 2020

(54) COMPOSITION WITH SUSTAINED ANTIMICROBIAL ACTIVITY

(71) Applicant: The Trustees of Columbia University in the City of New York, New York, NY (US)

(72) Inventors: Shanta M. Modak, Riveredge, NJ (US); Santoshkumar Hanmantrao Dongre, Maharashtra (IN)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/918,415

(22) Filed: Mar. 12, 2018

(65) Prior Publication Data

US 2018/0199574 A1  Jul. 19, 2018

Related U.S. Application Data

(63) Continuation of application No. 14/267,403, filed on May 1, 2014, which is a continuation of application No. PCT/US2012/063013, filed on Nov. 1, 2012.

(60) Provisional application No. 61/668,160, filed on Jul. 5, 2012, provisional application No. 61/583,505, filed on Jan. 5, 2012, provisional application No. 61/555,367, filed on Nov. 3, 2011.

(51) Int. Cl.
| | |
|---|---|
| *A01N 47/40* | (2006.01) |
| *A61K 8/34* | (2006.01) |
| *A61K 8/39* | (2006.01) |
| *A61K 8/41* | (2006.01) |
| *A61Q 17/00* | (2006.01) |
| *A61K 31/045* | (2006.01) |
| *A61K 31/14* | (2006.01) |
| *A61K 8/43* | (2006.01) |

(52) U.S. Cl.
CPC ............... *A01N 47/40* (2013.01); *A61K 8/34* (2013.01); *A61K 8/39* (2013.01); *A61K 8/416* (2013.01); *A61K 8/43* (2013.01); *A61K 31/045* (2013.01); *A61K 31/14* (2013.01); *A61Q 17/005* (2013.01)

(58) Field of Classification Search
CPC ........... A01N 47/40; A61K 8/43; A61K 8/39; A61K 8/416; A61K 8/34; A61K 31/045; A61K 31/14; A61Q 17/005
See application file for complete search history.

(56) References Cited

U.S. PATENT DOCUMENTS

| | | |
|---|---|---|
| 3,918,952 A | 11/1975 | Neumiller |
| 4,022,605 A | 5/1977 | Konya et al. |
| 4,049,802 A | 9/1977 | Fox, Jr. |
| 4,330,531 A | 5/1982 | Alliger |
| 4,404,197 A | 9/1983 | Fox, Jr. et al. |
| 4,563,485 A | 1/1986 | Fox, Jr. et al. |
| 4,579,731 A | 4/1986 | Fox, Jr. et al. |
| 4,581,028 A | 4/1986 | Fox, Jr. et al. |
| 4,612,337 A | 9/1986 | Fox, Jr. et al. |
| 4,723,950 A | 2/1988 | Lee |
| 4,859,359 A | 8/1989 | DeMatteo et al. |
| 4,867,898 A | 9/1989 | Spaulding et al. |
| 4,956,354 A | 9/1990 | Gutierrez |
| 4,975,217 A | 12/1990 | Brown-Skrobot et al. |
| 5,019,096 A | 5/1991 | Fox, Jr. et al. |
| 5,033,488 A | 7/1991 | Curtis et al. |
| 5,073,366 A | 12/1991 | Beck |
| 5,091,442 A | 2/1992 | Milner |
| 5,100,652 A | 3/1992 | Kross et al. |
| 5,135,747 A | 8/1992 | Faryniarz et al. |
| 5,180,605 A | 1/1993 | Milner |
| 5,200,194 A | 4/1993 | Edgren et al. |
| 5,209,251 A | 5/1993 | Curtis et al. |
| 5,261,421 A | 11/1993 | Milner |
| 5,310,546 A | 5/1994 | Douglas |
| 5,334,588 A | 8/1994 | Fox, Jr. et al. |
| 5,567,495 A | 10/1996 | Modak et al. |
| 5,614,538 A | 3/1997 | Nelson, Jr. |
| 5,616,338 A | 4/1997 | Fox, Jr. et al. |
| 5,772,640 A | 6/1998 | Modak et al. |
| 5,854,266 A | 12/1998 | Nelson, Jr. |
| 5,866,527 A | 2/1999 | Mertens |
| 5,891,422 A | 4/1999 | Pan et al. |
| 5,968,539 A | 10/1999 | Beerse et al. |
| 5,985,819 A | 11/1999 | Lu et al. |
| 5,985,918 A | 11/1999 | Modak et al. |
| 6,075,056 A | 6/2000 | Quigley, Jr. et al. |
| 6,083,208 A | 7/2000 | Modak et al. |

(Continued)

FOREIGN PATENT DOCUMENTS

| | | |
|---|---|---|
| CH | 654327 A5 | 2/1986 |
| DE | 202004018623 U1 | 4/2005 |

(Continued)

OTHER PUBLICATIONS

MMWR, https://www.cdc.gov/mmwr/PDF/rr/rr5116.pdf (Year: 2002).*
Block, S.S., "Disinfection, Sterilization, and Preservation; Fourth Edition," 1991, pp. Cover, 280-281 and 892, Publisher: Lea & Febiger.
Daily Med, "Antiseptic Skin Cleanser—chlorhexidine gluconate liquid, Drug Label Information," https://dailymed.nlm.nih.gov/dailymed/drugInfo.cfm?setid=5577ecbb-cf2c-45e1-a0fb-17df . . . , updated on Sep. 2012, retrieved on Jun. 24, 2016, pp. 1-2.
EPO: Extended Search Report, European Patent Application No. 12845196.0, dated Sep. 5, 2016, pp. 1-8.

(Continued)

*Primary Examiner* — Angela C Brown-Pettigrew
(74) *Attorney, Agent, or Firm* — Wolter Van Dyke Davis, PLLC; Timothy H. Van Dyke; Martha Cassidy

(57) ABSTRACT

Disclosed herein are compositions comprising benzyl alcohol, one or more cationic antimicrobial agent, and one or more emollient, the combination of which results in persistent antimicrobial activity after application to the skin. The compositions optionally further comprise an organic acid and/or a zinc salt, such as zinc gluconate, as an anti-irritant.

9 Claims, No Drawings

(56) References Cited

U.S. PATENT DOCUMENTS

| | | |
|---|---|---|
| 6,106,505 A | 8/2000 | Modak et al. |
| 6,120,758 A | 9/2000 | Siddiqui et al. |
| 6,258,368 B1 | 7/2001 | Beerse et al. |
| 6,270,811 B1 | 8/2001 | Fregonese |
| 6,280,758 B1 | 8/2001 | Warren et al. |
| 6,287,583 B1 | 9/2001 | Warren et al. |
| 6,312,675 B1 | 11/2001 | Deane |
| 6,319,958 B1 | 11/2001 | Johnson et al. |
| 6,323,166 B1 | 11/2001 | Kamiya |
| 6,348,501 B1 | 2/2002 | Holt et al. |
| 6,397,224 B1 | 5/2002 | Zubeldia et al. |
| 6,420,326 B1 | 7/2002 | Maile et al. |
| 6,451,748 B1 | 9/2002 | Taylor et al. |
| 6,537,955 B1 | 3/2003 | Raso et al. |
| 6,582,719 B2 | 6/2003 | Modak et al. |
| 6,616,922 B2 | 9/2003 | Taylor et al. |
| 6,630,163 B1 | 10/2003 | Murad |
| 6,632,784 B2 | 10/2003 | Massaux et al. |
| 6,635,676 B2 | 10/2003 | Baker, Jr. et al. |
| 6,696,399 B1 | 2/2004 | Chernin et al. |
| 6,699,825 B2 | 3/2004 | Rees et al. |
| 6,716,883 B1 | 4/2004 | Casper et al. |
| 6,753,305 B2 | 6/2004 | Raso et al. |
| 6,858,317 B2 | 2/2005 | Aamodt et al. |
| 6,921,745 B2 | 7/2005 | Yamada et al. |
| 6,951,833 B2 | 10/2005 | O'Neil |
| 6,969,522 B2 | 11/2005 | Bessette et al. |
| 7,247,295 B2 | 7/2007 | Schmaus et al. |
| 7,435,429 B2 | 10/2008 | Modak et al. |
| 7,563,461 B2 | 7/2009 | Modak et al. |
| 7,563,462 B2 | 7/2009 | Modak et al. |
| 7,572,469 B2 | 8/2009 | Santo et al. |
| 7,745,425 B2 | 6/2010 | Modak et al. |
| 7,829,029 B2 | 11/2010 | Zumeris et al. |
| 7,871,649 B2 | 1/2011 | Modak et al. |
| 7,985,773 B2 | 7/2011 | Greten et al. |
| 8,568,815 B2 | 10/2013 | Parkkinen |
| 8,932,624 B2 | 1/2015 | Modak et al. |
| 8,932,650 B2 | 1/2015 | Kross |
| 8,951,552 B2 | 2/2015 | Shalaby et al. |
| 9,511,040 B2 | 12/2016 | Modak |
| 2001/0010016 A1 | 7/2001 | Modak et al. |
| 2001/0024661 A1 | 9/2001 | Modak et al. |
| 2002/0064546 A1 | 5/2002 | Harris |
| 2002/0122876 A1 | 9/2002 | Modak et al. |
| 2002/0165130 A1 | 11/2002 | Johnson et al. |
| 2002/0173775 A1 | 11/2002 | Modak et al. |
| 2002/0192256 A1 | 12/2002 | Wu et al. |
| 2003/0113388 A1 | 6/2003 | Phan |
| 2003/0044451 A1 | 9/2003 | McGhee |
| 2003/0165546 A1 | 9/2003 | Resch et al. |
| 2003/0168077 A1 | 9/2003 | Brown et al. |
| 2003/0180233 A1 | 9/2003 | Anderson et al. |
| 2003/0195263 A1 | 10/2003 | Schmaus et al. |
| 2003/0213168 A1 | 11/2003 | Hesse et al. |
| 2004/0092482 A1 | 5/2004 | Gupta |
| 2004/0102429 A1 | 5/2004 | Modak et al. |
| 2004/0132667 A1 | 7/2004 | Lintner |
| 2004/0192551 A1 | 9/2004 | Bessette et al. |
| 2004/0247685 A1 | 12/2004 | Modak et al. |
| 2004/0253275 A1 | 12/2004 | Eini et al. |
| 2005/0019431 A1 | 1/2005 | Modak et al. |
| 2005/0026802 A1 | 2/2005 | Kilkenny et al. |
| 2005/0048139 A1 | 3/2005 | Modak et al. |
| 2005/0063939 A1 | 3/2005 | Ameer et al. |
| 2005/0187124 A1 | 8/2005 | Li et al. |
| 2005/0222276 A1 | 10/2005 | Schmaus et al. |
| 2005/0238602 A1 | 10/2005 | Modak et al. |
| 2006/0018867 A1 | 1/2006 | Kawasaki et al. |
| 2006/0051384 A1 | 3/2006 | Scholz et al. |
| 2006/0099237 A1 | 5/2006 | Modak et al. |
| 2006/0198800 A1 | 9/2006 | Dilallo et al. |
| 2006/0216246 A1 | 9/2006 | Belanger et al. |
| 2006/0233901 A1 | 10/2006 | Jamieson et al. |
| 2006/0293201 A1 | 12/2006 | Simon et al. |
| 2006/0293214 A1 | 12/2006 | Cheng et al. |
| 2007/0003538 A1 | 1/2007 | Madhyastha |
| 2007/0014823 A1 | 1/2007 | Iwata et al. |
| 2007/0020342 A1 | 1/2007 | Modak et al. |
| 2007/0027119 A1 | 2/2007 | Ahmed et al. |
| 2007/0190094 A1 | 8/2007 | Bessette et al. |
| 2007/0275070 A1 | 11/2007 | Ahmed et al. |
| 2007/0286813 A1 | 12/2007 | Toutounghi |
| 2008/0008729 A1 | 1/2008 | Swaine et al. |
| 2008/0038219 A1 | 2/2008 | Mosbaugh et al. |
| 2008/0063607 A1 | 3/2008 | Tamarkin et al. |
| 2008/0166314 A1 | 7/2008 | Jochim et al. |
| 2008/0226568 A1 | 9/2008 | Rozsa et al. |
| 2008/0234173 A1 | 9/2008 | Warr et al. |
| 2008/0253976 A1 | 10/2008 | Scott et al. |
| 2008/0260708 A1 | 10/2008 | Hall |
| 2008/0299220 A1 | 12/2008 | Tamarkin et al. |
| 2008/0311231 A1 | 12/2008 | Modak et al. |
| 2008/0317737 A1 | 12/2008 | Patel et al. |
| 2008/0318784 A1 | 12/2008 | Koo et al. |
| 2009/0004122 A1 | 1/2009 | Modak et al. |
| 2009/0028751 A1 | 1/2009 | Robbins |
| 2009/0029961 A1 | 1/2009 | Modak et al. |
| 2009/0221989 A1 | 1/2009 | Najafi et al. |
| 2009/0035228 A1 | 2/2009 | Modak et al. |
| 2009/0068255 A1 | 3/2009 | Yu et al. |
| 2009/0088358 A1 | 4/2009 | Roso et al. |
| 2009/0165812 A1 | 7/2009 | Resnick et al. |
| 2009/0175806 A1 | 7/2009 | Modak et al. |
| 2009/0191288 A1 | 7/2009 | Squires et al. |
| 2009/0300864 A1 | 12/2009 | Adkins et al. |
| 2010/0034871 A1 | 2/2010 | Mikkelsen et al. |
| 2010/0093595 A1 | 4/2010 | Holzhauer et al. |
| 2010/0140368 A1 | 6/2010 | De Lame et al. |
| 2010/0172847 A1 | 7/2010 | Modak et al. |
| 2010/0172848 A1 | 7/2010 | Modak et al. |
| 2010/0183524 A1 | 7/2010 | Zielinski et al. |
| 2010/0196494 A1 | 8/2010 | VanBeek |
| 2010/0216889 A1 | 8/2010 | Modak et al. |
| 2010/0234460 A1 | 9/2010 | Foret et al. |
| 2010/0248962 A1 | 9/2010 | Wilczynski et al. |
| 2010/0317743 A1 | 12/2010 | Macinga et al. |
| 2010/0323043 A1 | 12/2010 | Perla et al. |
| 2011/0028563 A1 | 2/2011 | Found |
| 2011/0070376 A1 | 3/2011 | Wales et al. |
| 2011/0142899 A1 | 6/2011 | Lagaron Abello et al. |
| 2012/0100231 A1 | 4/2012 | Perla et al. |
| 2012/0129950 A1 | 5/2012 | Macinga et al. |
| 2012/0171156 A1 | 7/2012 | Basketter et al. |
| 2012/0201902 A1 | 8/2012 | Modak et al. |
| 2012/0203211 A1 | 8/2012 | Weadock et al. |
| 2012/0207862 A1 | 8/2012 | Morre et al. |
| 2013/0230609 A1 | 9/2013 | Modak et al. |
| 2014/0079819 A1 | 3/2014 | Debaun et al. |
| 2014/0178447 A1 | 6/2014 | Modak et al. |
| 2014/0242198 A1 | 8/2014 | Modak et al. |
| 2014/0243417 A1 | 8/2014 | Modak et al. |
| 2014/0287072 A1 | 9/2014 | Modak et al. |
| 2014/0322147 A1 | 10/2014 | Modak et al. |

FOREIGN PATENT DOCUMENTS

| | | |
|---|---|---|
| DE | 202008002718 U1 | 7/2009 |
| EP | 0054205 A1 | 6/1982 |
| EP | 0106266 A2 | 4/1984 |
| EP | 0231080 A1 | 8/1987 |
| EP | 1108419 A1 | 6/2001 |
| EP | 1146112 A1 | 10/2001 |
| EP | 1206933 A1 | 5/2002 |
| EP | 1288285 A1 | 3/2003 |
| EP | 2775847 | 9/2014 |
| FR | 2771632 A1 | 6/1999 |
| FR | 2874928 A3 | 3/2010 |
| GB | 1060447 | 3/1967 |
| JP | 1997-323910 A | 12/1997 |
| JP | 2002-193717 A | 7/2002 |
| JP | 2002-370958 A | 12/2002 |
| JP | 2004-217615 A | 8/2004 |
| JP | 04250331 A | 9/2004 |

(56) References Cited

FOREIGN PATENT DOCUMENTS

| | | |
|---|---|---|
| JP | 2004-277554 A | 10/2004 |
| JP | 2004-322078 | 11/2004 |
| JP | 2006-225289 A | 8/2006 |
| JP | 2007-291049 A | 11/2007 |
| JP | 2010-83806 A | 4/2010 |
| JP | 2010-184987 A | 8/2010 |
| KR | 10-2004-077206 | 9/2004 |
| SU | 513676 A1 | 5/1976 |
| WO | 84/04456 A1 | 11/1984 |
| WO | 85/01208 A1 | 3/1985 |
| WO | 89/06962 A1 | 8/1989 |
| WO | 92/04029 A1 | 3/1992 |
| WO | 93/02717 A1 | 2/1993 |
| WO | 98/51273 A1 | 11/1998 |
| WO | 99/22718 A1 | 5/1999 |
| WO | 2000/015288 A1 | 3/2000 |
| WO | 00/65011 A1 | 11/2000 |
| WO | 01/72262 A2 | 10/2001 |
| WO | 01/91555 A2 | 12/2001 |
| WO | 02/22060 A1 | 3/2002 |
| WO | 2002/051464 A2 | 7/2002 |
| WO | 03/000303 A1 | 1/2003 |
| WO | 03/018498 A1 | 3/2003 |
| WO | 03/018743 A2 | 3/2003 |
| WO | 03/077856 A2 | 9/2003 |
| WO | 03/078367 A2 | 9/2003 |
| WO | 2004/004631 A2 | 1/2004 |
| WO | 2004/014416 A1 | 2/2004 |
| WO | 2006/010269 A1 | 2/2006 |
| WO | 2006/023349 A1 | 3/2006 |
| WO | 2006/099359 A2 | 9/2006 |
| WO | 2008/135085 A1 | 4/2007 |
| WO | 2007/069214 A2 | 6/2007 |
| WO | 2007/070795 | 6/2007 |
| WO | 2007/071089 A1 | 6/2007 |
| WO | 2007/077573 A1 | 7/2007 |
| WO | 2007/095041 A2 | 8/2007 |
| WO | 2007/101848 A1 | 9/2007 |
| WO | 2007/123790 A1 | 11/2007 |
| WO | 2007/126651 A2 | 11/2007 |
| WO | 2008/031087 A1 | 3/2008 |
| WO | 2008/031601 A1 | 3/2008 |
| WO | 2008/042197 A1 | 4/2008 |
| WO | 2008/061187 A1 | 5/2008 |
| WO | 2008/119841 A2 | 10/2008 |
| WO | 2008/135085 | 11/2008 |
| WO | 2008/154395 A1 | 12/2008 |
| WO | 2008/157847 A1 | 12/2008 |
| WO | 2009/062746 A2 | 3/2009 |
| WO | 2009/049208 A1 | 4/2009 |
| WO | 2010/091415 A1 | 8/2010 |
| WO | 2010/119369 A2 | 10/2010 |
| WO | 2011/002929 A1 | 1/2011 |
| WO | 2011/151835 A1 | 12/2011 |
| WO | 2012/017349 A2 | 2/2012 |
| WO | 2012/051204 A2 | 4/2012 |
| WO | 2012/109187 A1 | 8/2012 |
| WO | 2013/066403 A1 | 5/2013 |
| WO | 2013/103556 A1 | 7/2013 |
| WO | 2014/165854 A1 | 1/2014 |
| WO | 2014/092999 A1 | 6/2014 |
| WO | 2014/165046 A1 | 10/2014 |

OTHER PUBLICATIONS

EPO: Supplementary Partial Search Report, European Patent Application No. 12845196.0, dated May 17, 2016, pp. 1-6.
EPO: Supplementary Search Report, European Patent Application No. 12846062.3, dated Jan. 8, 2016, pp. 1-14.
EPO: Supplementary Search Report, European Patent Application No. 14763192.3, dated Jan. 5, 2017, pp. 1-7.
Jabra-Rizk, M.A., et al., "Effects of Farnesol on *Staphlyococcus aureus* Biofilm Formation and Antimicrobial Suspectibility," Antimicrobial Agents and Chemotherapy 2006, pp. 1463-1469, Publisher: American Society for Microbiology.
Watts, J. L., et al., "Evaluation of Test Dips with Excised Teats," Journal of Dairy Science 1984, pp. 2062-2065, vol. 67, Issue 9.
Anand, P., et al., "Biological activities of curcumin and its analogues (Congeners) made by man and Mother Nature," Biochemical Pharmacology 2008, pp. 1590-1611, vol. 76, No. 11, DOI: 10.1016/j.bcp.2008.08.008, Publisher: Elsevier Inc.
Ayliffe, G.A.J., et al., "Hand disinfection: A comparison of various agents in laboratory and ward studies," Journal of Hospital Infection 1988, pp. 226-243, vol. 11.
Bagamboula, C.F, et al., "Inhibitory effect of thyme and basil essential oils, carvacrol, thymol, estragol, linalool and p-cymene towards Shigella sonnei and S. flexneri," Food Microbiology 2004, pp. 33-42, vol. 21.
Baiju, N., et al., "Development of a novel surface disinfectant composition containing essential oils and fruit acid against nosocomial pathogens commonly associated with environmental surfaces," International Journal of Essential Oil Therapeutics 200, pp. 9-14, vol. 2.
Baratta, M.T., et al., "Antimicrobial and antioxidant properties of some commercial essential oils," Flavour and Fragrance Journal 1998, pp. 235-244, vol. 13.
Bettini, M., "Purification of Orange Peel Oil and Oil Phase by Vacuum Distillation," Functional Food Ingredients and Nutraceuticals, Processing Technologies 2006, pp. 157-172, Editor: John Shi, Publisher: CRC Press.
Bezic, N., et al., "Composition and antimicrobial activity of *Achillea clavennae* L. essential oil." Phytother. Res. 2003, pp. 1037-1040, vol. 17.
Bio Source Naturals, "Lemongrass Essential Oil: (*Cymbopogon citratus*)," http://www.biosourcenaturals.com/lemongrass-essential-oil.htm, retrieved on Apr. 5, 2015, pp. 1-2.
Bion, "Acne—Acne Treatment Products," http://www.bion-research.com/acne_treatment_products.htm, downloaded on Mar. 3, 2008, pp. 1-3.
Bion, "Moderate to Severe Acne," downloaded on Mar. 3, 2008, http://www.bion-research.com/moderate-to- severe acne.htm, pp. 1-5.
Biosecur Lab, "Biosecur Product Line Receives Self-Affirmed Gras Status for Use as an antioxidant and Nutrient Supplement", News Release dated Mar. 8, 2011, pp. 1-2.
Brehm-Stecher, B.F. and Jonson, E.A., "Sensitization of *Staphylococcus aureus* and *Escherichia coli* to antibiotics by the sesquiterpenoids nerolidol, famesol, bisabolol, and apritone," Antimicrobial Agents and Chemotherapy 2003, pp. 3357-3360, vol. 47, No. 10.
Cancio, L.C., "Burn wound infections," Surgical Treatment: Evidence-Based and Problem-Oriented 2001, pp. 1-20, Editors: Holzheimer, R.G. and Mannick, J.A.
Chalchat, J.C. et al, "Chemical Composition of Essential Oil of *Calendula officinalis* L. (Pot Marigold)," Flavour and Fragrance Journal 1991, pp. 189-192, vol. 6.
Chang, S., et al., "Resources and bioactive substances from Taiwania (*Taiwania cryptomerioides*)," J. Wood Sci 2003, pp. 1-4, vol. 49, Publisher: The Japan Wood Research Society.
Chemical Book, "8015-73-4(Basil oil) Product Description," http://www.chemicalbook.com/ChemicalProductProperty_US_CB3405198.aspx, retrieved on Jul. 1, 2015, pp. 1-2.
Choudhary, V.R., et al., "Solvent-free selective oxidation of benzyl alcohol and benzaldehyde by tert-butyl hydroperoxide using Mn04-exchanged Mg—Al-hydrotalcite catalsysts," Catalysis Letters 2003, pp. 229-233, vol. 86, No. 4.
Collins, D.A., "A review of alternatives to organophosphorus compounds for the control of storage mites," Journal of Stored Products Research 2006, pp. 395-426, vol. 42, Publisher: Elsevier Ltd.
Cowan., M. M., "Plant product as antimicrobial agents", Clinical Microbiology Reviews 1999, pp. 564-582, vol. 12, No. 4, Publisher: American Society for Microbiology.
Daily Med, "Antiseptic Skin Cleanser—chlorhexidine gluconate liquid, Drug Label Information," https://dailymed.nlm.nih.gov/dailymed/drugInfo.cfm?setid=5577ecbb-cf2c-45e1-a0fb-17df . . . , updated on 09/12, retrieved on Jun. 24, 2016, pp. 1-2.

(56) References Cited

OTHER PUBLICATIONS

De Abreu Gonzaga, W., et al., "Composition and antibacterial activity of the essential oils from Zanthoxylum rhoifolium," Planta Med. 2003, pp. 773-775, vol. 69.
El-Zemity, S.R. and Ahmed, S.M., et al., "Antifungal activity of some essential oils and their major chemical constituents against some phytopathogenic fungi," Journal of Pest Control and Enviromental Science 2005, pp. 61-72, vol. 13, No. 1.
EPO: Extended Search Report, European Patent Application No. 08780771.5, dated Jan. 2, 2013, pp. 1-6.
EPO: Office Action, European Patent Application No. 10794733.5, dated Dec. 2, 2014, pp. 1-9.
EPO: Supplementary Partial European Search Report, European Patent Application No. 12846062.3, dated Aug. 12, 2015, pp. 1-8.
Esoteric Oil, "Orange essential oil (sweet information)," http/www.essentialoils.co.za/essential-oils/orange.htm, retrieved on Jul. 15, 2012, p. 1.
Esoteric Oils, "Lemongrass essential oil information," http/www.essentialoils.co.za/essential-oils/lemongrass.htm, downloaded on Jul. 15, 2012, p. 1.
Fang, C., et al., "Prospective clinical study of Hydron, a synthetic dressing, in delivery of an antimicrobial drug to second-degree burns," J Burn Care Rehabil. 1987, pp. 206-209, vol. 8, No. 3.
Fox, C.L., et al., "Comparative evaluation of zinc sulfadiazine and silver sulfadiazine in burn wound infection," J Burn Care Rehabil. 1990, pp. 112-117, vol. 11, No. 2.
Gaonkar, T.A., et al., "An alcohol hand rub containing a synergistic combination of an emollient and preservatives: prolonged activity against transient pathogens", Journal of Hospital Injection 2005, pp. 12-18, vol. 59.
Gaonkar, T.A., et al., "In vivo efficacy of an alcohol-based surgical hand disinfectant containing a synergistic combination of ethylhexylglycerin and preservatives," Journal of Hospital Injection 2006, pp. 412-417, vol. 63.
Garcia, C.C., et al., "Virucidal activity of essential oils from aromatic plants of San Luis, Argentina," Phytother. Res. 2003, pp. 1073-1075, vol. 19, No. 9.
Gemeda, N., "Effect of essential oils on aspergillus spore germination, growth and mycotoxin production: a potential source of botanical food preservative", Asian Pacific Journal of Tropical Biomedicine 2014, pp. S373-S381, vol. 4 (Suppl).
Gershon, H. And Shanks, L., "Antifungal Properties of n-Alkanols, a, w-n-Alkanedoils, and w-Chloro-a-alkanols", J Pharm. Sci. 1980, pp. 381-384, vol. 64, No. 4.
Goren, A.C., et al., "Analysis of essential oil of *Coridothymus capitatus* (L.) and its antibacterial and antifungal activity," Z. Naturforsch. 2003, pp. 687-690, vol. 58, No. 9-10.
Gupta, V.K., "Third Party Observation," filed in U.S. Appl. No. 12/694,119, filed Aug. 7, 2010, pp. 1-35.
Gupta, V.K., "Third Party Observation," filed in U.S. Appl. No. 12/694,141, filed Jul. 19, 2010, pp. 1-26.
Hajhashemi, V., et al., "Anti-inflammatory and analgesic properties of the leaf extracts and essential oil of *Lavandula angustifolia* Mill." J. Ethnopharmacol. 2003, pp. 67-71, vol. 89.
Hazan, R., et al., "Benzoic Acid, a Weak Organic Acid Food Preservative, Exerts Specific Effects on Intracellular Membrane Trafficking Pathways in *Saccharomyces cerevisiae*" Appl. Environ. Microbial. 2004, pp. 4449-4457, vol. 70, No. 8.
IP Australia: Patent Examination Report No. 1, Australian Patent Application No. 2012332495, dated Jun. 10, 2016, pp. 1-3.
ISA/US: International Search Report and Written Opinion, International Patent Application No. PCT/US2012/63013, dated Jan. 4, 2013; pp. 1-8.
ISA/US: International Search Report and Written Opinion, International Patent Application No. PCT/US2012/052793, dated Nov. 19, 2012, pp. 1-14.
ISA/US: International Search Report and Written Opinion, International Patent Application No. PCT/US14/29486, dated Oct. 10, 2014, pp. 1-14.
ISA/US: International Search Report and Written Opinion, International Patent Application No. PCT/US15/62454, dated Feb. 9, 2016, pp. 1-12.
ISA/US: International Search Report and Written Opinion, International Patent Application No. PCT/US2012/037135, dated Oct. 16, 2012, pp. 1-13.
ISA/US: International Search Report and Written Opinion, International Patent Application No. PCT/US2013/071731, dated Feb. 12, 2014, pp. 1-11.
JPO: Rejection, Japanese Patent Application No. 2014-539926, dated Jan. 19, 2016, 17 pages.
Judzentiene, A., et al., "Characterisitcs of essential oil composition in the needles of young Scots pine (*Pinus sylvestris* L.) stands growing along an aerial ammonia gradient," CHEMIJA 2006, pp. 67-73, vol. 17, No. 4.
Keeven, J., et al., "Evaluating the preservative effectiveness of RGP lens care solutions," CLAO J. 1995, pp. 238-241, vol. 21, No. 4.
Klaric, M.S., et al., "Antifungal activity of thyme (*Thymus vulgaris* L.) essential oil and thymol against moulds from damp dwellings," Letters in Applied Microbiology 2007, pp. 36-42, vol. 44, No. 1.
Komthong, P., et al., "Ascending bubble extraction of terpenes from freshly squeezed orange juice", Food Research International 2006, pp. 53-58, vol. 39.
Kumar, A., et al., "Assessment of *Thymus vulgaris* L. essential oil as a safe botanical preservative against post harvest fungal infestation of food commodities", Innovative Food Science and Emerging Technologies 2008, pp. 575-580, vol. 9, No. 4.
Kupferwasser, L.I., et al., "Acetylsalicylic Acid Reduces Vegetation Bacterial Density, Hematogenous Bacterial Dissemination, and Frequency of Embolic Events in Experimental *Staphylococcus aureus* Endocarditis Through Antiplatelet and Antibacterial Effects," Circulation 1999, pp. 2791-2797, vol. 99, Publisher: American Heart Association, Inc.
Kupferwasser, L.I., et al., "Salicylic Acid Attenuates Virulence in Endovascular Infections by Targeting Global Regulatory Pathways in *Staphylococcus aureus*," J. Clin. Invest. 2003, pp. 222-233, vol. 112.
Kurita, N. and Koike, S., "Synergistic Antimicrobial Effect of Ethanol, Sodium Chloride, Acetic Acid and Essential Oil Components," *Agricultural Biology Chemistry 1983*, pp. 67-75, vol. 47, No. 1.
mercola.com, "*Lemoncirass Oil: Lighten Up Your Mood with This All-Around Oil*," http://articles.mercola.com/herbal-oils/lemongrass-oil.aspx, printed on Mar. 26, 2015, pp. 1-4.
Minami, M., et al., "The inhibitory effect of essential oils on herpes simplex virus type-1 replication in vitro," Microbial Immunol. 2003, pp. 681-684, vol. 47, No. 9.
Mintel Global New Products Database 2008, "Antibacterial Wet Wipes," retrieved from the Internet: URL:www.gnQd.com, retrieved on Sep. 24, 2013, pp. 1-2.
Mintel Global New Products Database 2010, "Sheer Moisturizer Hand Sanitizer", retrieved from the Internet: URL:www.gn.Qd.com on Aug. 24, 2013, pp. 1-4.
Morganics, "Skin Care," Morganics, retrieved on Jul. 1, 2015, www.morganics.com/store/page8.html, p. 1.
Nannapaneri, R., et al., "Antimicrobial activity of commercial citrus-based natural extracts against *Escherichia coli* 0157:H7 isolates and mutant strains", Foodborne Pathogens and Disease 2008, pp. 695-699, vol. 5, No. 5, Publisher: May Ann Liebert, Inc.
Nazer, A.I., et al., "Combinations of food antimicrobials at low levels to inhibit the growth of *Salmonella* sv. Typhimurium: a synergistic effect?," Food Microbiology 2005, pp. 391-398, vol. 22.
Nerio, L.S., et al., "Repallant activity of essential oils: A review", Biosource Technology 2010, pp. 372-378, vol. 101.
Panchatcharam, M., et al., "Curcumin improves wound healing by modulating collagen and decreasing reactive oxygen species," Molecular and Cellular Biochemistry 2006, pp. 87-96, vol. 290, Publisher: Springer.
Paranagama, P.A., et al., "Fungicidal and anti-aflatoxigenic effects of the essential oil of *Cymbopogon citratus* (DC.) *Stapf.* (lemongrass) against Aspergillus flavus Link. isolated from stored rice," Lett. Appl. Microbial. 2003, pp. 86-90, vol. 37.

(56) References Cited

OTHER PUBLICATIONS

Pommier, P., et al., "Phase III Randomized Trial of Calendula Officinalis Compared With Trolamine for the Prevention of Acute Dermatitis During Irradiation for Breast Cancer," J Clin Oncol 2004, pp. 1447-1453, vol. 22, No. 8.
Prabuseenivasan, S., et al., "In vitro antibacterial activity of some plant essential oils", BMC Complementary and Alternative Medicine 2006, pp. 1-8, vol. 6, No. 39.
Reagor, L., et al., "The Effectiveness of Processed Grapefruit-Seed Extract as an Antibacterial Agent: I. An In Vitro Agar Assay," The Journal of Alternative and Complementary Medicine 2002, pp. 325-332, vol. 8, No. 3.
Schuhmacher, S., et al., "Virucidal effect of peppermint oil on the enveloped viruses herpes simplex virus type 1 and type 2 in vitro," Phytomedicine 2003, pp. 504-510, vol. 10.
Sharma, A., "Third Party Observation," filed in Canadian Patent Application No. 2769627, Jun. 25, 2014, pp. 1-39.
Shin, S., "Anti-Aspergillus activities of plant essential oils and their combination effects with ketoconazole or amphotericin B", Arch. Pharm. Res. 2003, pp. 389-393, vol. 26, No. 5.
Silva, J., "Analgesic and anti-inflammatory effects of essential oils of Eucalyptus," J. Ethnopharmacol. 2003, pp. 277-283, vol. 89.
Song, Q., et al., "Volatiles from Ficus hispida and their attractiveness to fig wasps", Journal of Chemical Ecology 2001, pp. 1929-1942, vol. 27, No. 10.
Subba, M.S., et al., "Antimicrobial Action of Citrus Oils," J. Food Sci. 1967, pp. 225-227, vol. 32, No. 2.
Table of Acids with Ka and pKa Values, Chem 1A, B, C Lab Manual and Zumdahl 6th Edition, Appendix 5, http://clas.sa.ucsb.edu/staff/Resource%20folder/Chem109ABC/Acid,%20Base%20Strength/Table%20of%20Acids%20w%20Ka s%20and%20pKas.pdf, copy downloaded on Sep. 28, 2015.
Tayyem, R.F., et al., "Curcumin Content of Turmeric and Curry Powders", Nutrition and Cancer 2006, pp. 126-131, vol. 55, No. 2, Publisher: Lawrence Erlbaum Associates, Inc.
The Lubrizol Corporation, "Tecophilic TPU—LifeScience Polymers," https://web.archive.org/web/20140923074123/http:1/www.lubrizol.com/LifeScience/Prod ucts/Tecophilic.html; Sep. 23, 2014 [downloaded from internet on Jan. 12, 2016], pp. 1-2.
The Merck Index, "02322. Citral," 2011, pp. 1-2, 14th Edition, Publisher: Merck Sharp & Dohme Corp.
Valero, M. and Salmeron, M.C., "Antibacterial activity of 11 essential oils against Bacillus cereus in tyndallized carrot broth," Int. J. Food Microbial. 2003, pp. 73-81, vol. 85.
Velluti, A., et al., "Inhibitory effect of cinnamon, clove, lemongrass, oregano and palmarose essential oils on growth and fumonisin B1 production by Fusarium proliferatum in maize grain," Int. J. Food Microbial. 2003, pp. 145-154, vol. 89.
Wilson, N.D., et al., "The quantification of citral in lemongrass and lemon oils by near-infrared spectroscopy", Journal of Pharmacy and Pharmacology 2002, pp. 1257-1263, vol. 54, Publisher: The Authors.
Zeus Quimica, S.A, "Zemea Propanediol—From Corn to Cosmetics . . . Formulate with Nature," downloaded on Jun. 24, 2015, p. 1.
Zhang, Z., et al., "Antifungal Activities of Major Tea Leaf Volatile Constituents toward Colletorichum Camelliae Massea," Journal of Agricultural and Food Chemistry 2006, pp. 3936-3940, vol. 54.
Abu Bakr Mohammad, Bin Zakariyya Al-Razi; Kitaab-al-Haawi-fil-Tibb, vol. ii (9th century AD), Dayerah-Al-Ma'aarof Is,amoa. Juderabad. 1976 AD p. 434.
Cakrapanidattah; Cakradattah—Translated by Indradeva Tripathi; Chaukhamba Sanskrit Samsthan (Varanasi), Ed. 4th 2002, p. 260.
Khazaain-ai-Advia vol. JII (20th century Ad), Mohammad Najmul Ghani Khan, Nadecm Yunus Printer/Sheikh Mohd Basheer & Sons, Lahore, 1926 AD p. 1050.
Khazaain-al-Advia vol. II (20th century Ad), Mohammad Najmul Ghani Khan, Nadeem Yunus Printer/Sheikh Mohd Basheer & Sons, Lahore, 1911 AD p. 342-343.
Khazaain-al-Advia vol. II (20th century AD), Mohammad Najmul Ghani Khan, Nadeem Yunus Printer/Sheikh Mohd Basheer & Sons, Lahore, 1911 AD p. 657.
Khazaain-al-Advia, vol. I (20th century AD) Mohammad Najmul Ghani Khan; Nadeem Yunus Printer/Sheikh Mohd Basheer & Sons, Lahore, 1911 AD p. 669.
Kitaab-al-Haawi-fil-Tibb, vol. IX (9th century AD), Abu Bakr Mohammad Bin Zakariyya Al-Razi; Dayerah-al-Ma'aarif Usmania, Hyberabad, (First Edition) 1960 AD p. 194.
Kitaab-al-Umdah-fil-Jeraahat, Part I (13th century AD), Aminud-daulah Abul Farj Ibn Al-Quff Maseehi; Dayerah-al-Ma'aarif Usmania, Hyberabad, 1937 AD p. 234-235.
Mohammad Azam Khan; Muheet Azam vol. II (Part II) (19th century AD), Matba Nizami, Kanpur, 1898 AD p. 3.
Mohammad Azam Khan; Muheet-e-Azam vol. I (19th century AD), Matba Nizami, Kanpur, 1896 AD p. 257.
Mohammad Azam Khan; Muheet-e-Azam vol. III (19th century AD), Matba Nizami, Kanpur, 1887 AD p. 261.
Mohammad Najmul Ghani Khan; Qaraabaadeen Najm-al-Ghani (20th century AD), Munshi Nawal Kishore, Lucknow, (Second Edition) 1928 AD p. 566.
Mohammad Shareef Khan; Ilaaj-al-Amraaz (18th centruy AD), Afzal-al-Matabe, Barqi Press, Delhi, 1921 AD p. 357.
Mohammad Azam Khan; Muheet-e-Azam vol. III (19th century Ad), Matba Nizami Kanpur, 1887 AD p. 69.
Mohammad Azam Khan; Muheet-e-Azam, vol. I (191 century Ad), Matba Nizami, n Kanpur, 1896 AD p. 197.
Mohammad Najmul Ghani Khan; K.hazaain-al-Advia, vol. III (20th century AD), Nadeem Yunus Printer/Sheikh Mohd Basheer & Sons, Lahore, 1926 AD p. 568.
Mohammad Najmul Ghani Khan; Khazaain-al-Advia, vol. II (20th century AD), Nadeem Yunus Printer/Sheikh Mohd Basheer & Sons, Lahore, 1911 AD p. 656.
Mohammad Najmul Ghani Khan; Khazaain-al-Advia, vol. II (20th century Ad), Nadeem Yunus Printer/Sheikh Mohd Basheer & Sons, Lahore, 1911 AD p. 657.
Mohammad Shareef Khan; Ilaaj-al-Amraaz (18th centruy AD), Afzal-al-Matabe, Barqi Press, Delhi, 1921 AD p. 335.
Qaraabaadeen Najm-al-Ghani (20th century AD), Mohammad Najmul Ghani Khan, Munshi Nawal Kishore, Lucknow, (Second Edition) 1928 AD p. 492.
Samgadharacarya; Saringadhara Samhita—Translated by Smt. Shailaja Srivastava: Chaukhamba Orientalia, Varansai, Edn. 2nd, 1998. [Time of origin 13th century] pp. 431-432.
Siddhayogasamgrahah—Compiled by Yadavji Trikamji Acharya, Sri Baidyanath Ayurved Bhawan, Allahabad, Edn. 1st 1978 pp. 131-132.
Sodhalanighantauh—(Namasamgraha Va Gunasamgraha) Sodhala; Edited by P.V. Sharma, Oriental Institute, Broda, Edn 1st 1978 p. 116.
Susruta; Susruta Samhita—Edited & translated by P.V. Sharma, vol. III: Chaukhamba Visvabharati, Varanasi, Edn. 1st, 2001. [Time of origin 1000 BC 5th century] p. 10.
Vagabhata; Astanga Hrdaya—(commentary by Arunadutta) edited by Bhisagacarya Harisastri Paradakara Vaidya; Chaukhamba Orientalia, Varanasi, edn. 8th, 1998 [Time of origin 5th century] p. 890.
Ziya Al-Din Abdullah Ibn Al-Baitar; al-Jaam'e-li-Mufradaat-al-Advia-wal Aghzia, vol. II (13th century AD), Matba Amra, Cairo, Egypt, 1874 AD p. 84.
Ziya Al-Din Abdullah Ibn Al Baitar; Al-Jaam'e-li-Mufradaat-al-Advia-wal Aghzia, vol. IV (13th century AD), Matba Amra, Cario, Egypt, 1874 AD p. 57.
Adesina et al., "Prevention of Bacterial Biofilms Formation on Urinary Catheter by Selected Plant Extracts," Pak. J. Biol. Sci., 2015, pp. 67-73, vol. 18(2).
Drekonja et al., "Antimicrobial Urinary Catheters: a systematic review," Expert Rev. Med. Devices, 2008, pp. 495-506, vol. 5(4).
Gaonkar, T.A., et al., "Efficacy of a Silicone Urinary Catheter Impregnated with Chlorhexidine and Triclosan against Colonization with Proteus mirabilis and Other Uropathogens," Infection Control & Hospital Epidemiology, 2007, pp. 596-598, vol. 28.
Gaonkar, T.A., et al.,"Evaluation of the Antimicrobial Efficacy of Urinary Catheters Impregnated with Antiseptics in an In Vitro Urinary Tract Model," Infection Control & Hospital Epidemiology, 2003, pp. 506-513, vol. 24(7).

(56) References Cited

OTHER PUBLICATIONS

Islas et al., "Singly and Binary Grafted Poly(vinyl chloride) Urinary Catheters that Elute Ciprofloxacin and Prevent Bacteria Adhesion," Int. J. Pharm, 2015, pp. 20-28, vol. 488.

Leuck et al., "Safety and efficacy of a novel silver-impregnated urinary catheter system for preventing catheter-associated bacteriuria: a pilot randomized clinical trial," Am J Infect Control, 2015, pp. 260-265, vol. 3.

Malic, S., et al., "Biocide activity against urinary catheter pathogens," Antimicrob Agents Chemother, 2014, pp. 1192-1194, vol. 58:2.

Margel et al., "Nitric oxide charged catheters as a potential strategy for prevention of hospital acquired infections," PLoS One, 2017, p. e0174443, vol. 12:4.

Mody et al., "Enhancing Resident Safety by Preventing Healthcare-associated Infection: a national initiative to reduce catheter-associated urinary tract infections in nursing homes," Clin. Infect. Dis, 2015, pp. 86-89, vol. 61.

Pickard, et al., "Antimicrobial catheters for reduction of symptomatic urinary tract infection in adults requiring short-term catheterisation in hospital: a multicentre randomised controlled trial," Lancet, 2012, pp. 192-735, vol. 382.

Sladjana, et al., "Biocide Activity against Urinary Catheter Pathogens," Antimicrob. Agents Chemother., 2014, pp. 1192-1194, vol. 58.

Thallinger et al., "Cellobiose Dehydrogenase Functionalized Urinary Catheter as Novel Antibiofilm System," J. Biomed Mater. Res. Part B, 2016, pp. 448-1456, vol. 104B.

Thallinger et al., "Preventing microbial colonisation of catheters: antimicrobial and antibiofilm activities of cellobiose dehydrogenase," International Journal of Antimicrobial Agents, 2014, pp. 402-408, vol. 44.

Thomas et al., "Inhibitory Effect of Silver Nanoparticle Fabricated Urinary Catheter on Colonization Efficiency of Coagulase Negative Staphylococci," J. Photochem. Photobiol. B, 2015, pp. 68-77, vol. 149.

\* cited by examiner

COMPOSITION WITH SUSTAINED ANTIMICROBIAL ACTIVITY

PRIORITY CLAIM

The present application is a continuation of U.S. patent application Ser. No. 14/267,403, filed May 1, 2014 which is a continuation of International Application No. PCT/US12/063013, filed Nov. 1, 2012, which claims priority to U.S. Provisional Patent Application Ser. No. 61/555,367, filed Nov. 3, 2011, U.S. Provisional Patent Application Ser. No. 61/583,505, filed Jan. 5, 2012, and U.S. Provisional Patent Application Ser. No. 61/668,160, filed Jul. 5, 2012, to each of which priority is claimed and all of which are incorporated herein by reference in their entireties.

1. INTRODUCTION

Disclosed herein are compositions comprising benzyl alcohol, a cationic antimicrobial agent, and an emollient, the combination of which results in persistent antimicrobial activity when applied to the skin.

2. BACKGROUND

Hand hygiene guidelines for healthcare personnel published by the Centers for Disease Control and Prevention recommend that alcohol-based hand gels and foams be used routinely, with intermittent thorough hand washing with soaps throughout the day. Studies have shown that the rate of compliance by the healthcare workers with the hand washing guidelines is lower than 50% partly because of the possibility/fear of skin irritation with the frequent use of soaps and partly due to lack of time. This problem could be addressed by the development of soaps and other skin-care products that have sufficient residual antibacterial activity on the skin to inactivate newly introduced bacteria.

3. SUMMARY

Disclosed herein are compositions comprising benzyl alcohol, one or more cationic antimicrobial agent, and one or more sesquiterpenoid and/or emollient solvent, the combination of which results in persistent antimicrobial activity after application to the skin. The compositions optionally further comprise an organic acid and/or one or more zinc salt as an anti-irritant.

In certain non-limiting embodiments, the composition comprises a synergistic combination of benzyl alcohol and one or more cationic antimicrobial agent such as a biguanide and/or a quaternary ammonium compound.

In certain non-limiting embodiments, the emollient is farnesol or dipropylene glycol. Without being limited by any theory, it is believed that such emollients enhance penetration of antimicrobial agents into the superficial layer of the skin, thereby prolonging their action.

The compositions disclosed herein may be used as soaps, hand sanitizers, creams, lotions, and splashes and may optionally be comprised in wipes.

Also provided is a method of providing a skin surface with a persistent antimicrobial activity, comprising treating the skin surface with a composition as described herein.

4. DETAILED DESCRIPTION

For clarity and not by way of limitation the detailed description is divided into the following subsections:
(i) benzyl alcohol;
(ii) antimicrobial agents;
(iii) sesquiterpenoids;
(iv) emollient solvents;
(v) organic acids;
(vi) additional components; and
(vii) compositions/methods of use.

"About" as that term is used herein means ±10% of the recited value.

"Persistent antimicrobial activity" is antimicrobial activity that is retained after the initial exposure to the composition, although not necessarily at the same level. In non-limiting embodiments, use of the composition results in topical antimicrobial activity for at least one hour or at least two hours or at least four hours following exposure to the composition. In specific non-limiting embodiments, the antimicrobial activity remaining after one hour is a log 10 reduction in colony forming units of at least 0.5, or at least 1, or at least 1.5, for example as determined by tests set forth below in section 5. In other specific non-limiting embodiments, the antimicrobial activity remaining after two hours is a log 10 reduction in colony forming units of at least 0.5, or at least 1, or at least 1.5, for example as determined by tests set forth below in section 5.

4.1 Benzyl Alcohol

The compositions disclosed herein comprise benzyl alcohol, at a concentration (percent weight/weight, "% w/w") between about 0.1 and about 5% w/w, or between about 0.1 and about 3% w/w, or between about 1.0 and about 3% w/w; or between 0.5 and 2% w/w. In specific non-limiting embodiments the benzyl alcohol is plant-derived.

In certain, non-limiting embodiments, the compositions disclosed herein comprise benzyl alcohol, at a concentration (percent weight/weight, "% w/w") between about 0.05 and about 5% w/w; or between about 0.05 and about 4.5% w/w; or between about 0.05 and about 4% w/w; or between about 0.05 and about 3.5% w/w; or between about 0.05 and about 3% w/w; or between about 0.05 and about 2.5% w/w; or between about 0.05 and about 2% w/w; or between about 0.05 and about 1.5% w/w; or between about 0.05 and about 1% w/w; or between about 0.05 and about 0.5% w/w; or between about 0.05 and about 0.45% w/w; or between about 0.05 and about 0.4% w/w; or between about 0.05 and about 0.35% w/w; or between about 0.05 and about 0.3% w/w; or between about 0.05 and about 0.25% w/w; or between about 0.05 and about 0.2% w/w; or between about 0.05 and about 0.15% w/w; or between about 0.05 and about 0.1% w/w; or between about 0.1 and about 0.5% w/w; or between about 0.1 and about 0.45% w/w; or between about 0.1 and about 0.4% w/w; or between about 0.1 and about 0.35% w/w; or between about 0.1 and about 0.3% w/w; or between about 0.1 and about 0.25% w/w; or between about 0.1 and about 0.2% w/w; or between about 0.1 and about 0.15% w/w.

4.2 Antimicrobial Agents

The compositions disclosed herein comprise one or more cationic antimicrobial agent. In certain non-limiting embodiments, the cationic antimicrobial agent(s) is (are) selected from the group consisting of quaternary ammonium antimicrobial compounds, antimicrobial biguanides, and combinations thereof. Quaternary ammonium antimicrobial compound, where present, is at a concentration between about 0.05 and 1% w/w, or between about 0.05 and about 0.5% w/w, or between about 0.1 and about 0.3% w/w, or between 0.1 and 0.23% w/w (if more than one species of quaternary ammonium antimicrobial compound is present, the foregoing are the concentration ranges of the total amount of all species present). Antimicrobial biguanide, where present, is at a concentration between about 0.05 and about 3.0% w/w, or between about 0.05 and 1.5% w/w, or between about 0.05 and about 1.0% w/w, or between about 0.05 and about 0.8% w/w, or between 0.05 and 0.5% w/w, or about 0.4% w/w; if more than one species of biguanide is present, the foregoing are the concentrations/ranges of the total amount of all species present.

Non-limiting examples of quaternary ammonium antimicrobial compounds that may be used include benzalkonium chloride (BZK), benzethonium chloride (BZT), dequalinium chloride, alkyldimethylbenzylammonium chloride, cetyl pyridinium chloride, methylbenzethonium chloride, cetalkonium chloride, cetrimonium chloride, cetyl trimethyl ammonium bromide (cetrimide) dofanium chloride, tetraethylammonium bromide, domiphen bromide, and combinations thereof.

Non-limiting examples of biguanides that may be used include chlorhexidine, as a free base or salt, polyhexamethylene biguanide ("PHMB"), alexidine, polyaminopropyl biguanide (e.g., Cosmocil CQ), and combinations thereof. Chlorhexidine salts that may be used include but are not limited to the following: chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine mono-diglycolate, chlorhexidine dilactate, chlorhexidine di-.alpha.-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, chlorhexidine embonate, and combinations thereof.

The compositions may further comprise one or more antimicrobial agent that is not a cationic antimicrobial agent. Non-limiting examples of such additional agents include triclosan, parachlorometaxylenol ("PCMX"), chloroeresol, chlorxylenol, benzyl alcohol, bronopol, chlorbutanol, ethanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylene, foscarnet, miconazole, fluconazole, itriconazole, ketoconazole, povidone iodine, combinations thereof and pharmaceutically acceptable salts thereof. For example, but not by way of limitation, phenoxyethanol, where present, may be at a concentration between about 0.1 and about 1% w/w, and triclosan, where present, may be at a concentration between about 0.025 to about 2% w/w, or between 0.15 and 1% w/w.

Another non-limiting example of an antimicrobial which may be used is iodopropynylbutyl carbamate (IPBC; Germall plus), for example at a concentration between 0.05 and 2% w/w.

4.3 Sesquiterpenoids

Compositions disclosed herein may comprise one or more sesquiterpenoid selected from the group consisting of farnesol, nerolidol, bisabolol, apritone and combinations thereof. Where present, the sesquiterpenoid (e.g. farnesol) is at a concentration between about 0.1 and about 4% w/w, or between about 0.1 and about 3% w/w, or between about 0.3 and about 3% w/w, or between about 1 and 3% w/w, or between about 0.1 and 0.3% w/w; or between about 0.5 and about 4% w/w, or between about 0.5 and 3% w/w; or between about 0.5 and 0.3% w/w.

4.4 Emollient Solvents

Compositions disclosed herein may comprise one or more emollient solvent selected from the group consisting of dipropylene glycol, diglycerol, ethyl hexyl glycerin and combinations thereof. Dipropylene glycol or diglycerol, where present, is at a concentration of between about 0.1 and 10% w/w, or between about 1 and about 5% w/w, or between 0.2 and 7% w/w, or between 0.1 and 4% w/w, or between 0.2 and 5% w/w; or ethyl hexyl glycerin where present, is at a concentration between about 0.3 and about 4% w/w, or between about 0.3 and 3% w/w, or between about 0.5 and about 3% w/w, or between 1 and 3% w/w, or between 0.5 and 1.0% w/w.

Additional compounds with emollient properties that may optionally be comprised in the compositions include, for example, butylene glycol, pentylene glycol, a $C_3$-$C_{12}$ alkanediol, a $C_5$-$C_{10}$ alkanediol, butanediol, pentanediol, hexanediol, octanediol, Symdiol™, emu oil, grapeseed oil, olive oil, caprylic/capric triglyceride, panthenol, lauric alcohol, propylene glycol, glycerin, isopropyl myristate and combinations thereof. In non-limiting examples, alkanediol may be present at a concentration between about 0.5 and about 2.0% w/w, or between about 0.5 and about 1.0% w/w, or between about 0.2 and about 2% w/w, or between about 0.2 and about 1.0% w/w; octanediol may be at a concentration between about 0.5 and about 2% w/w, or between about 0.5 and about 1.0% w/w; and butylene glycol may be present at a concentration between about 0.5 and about 3% w/w.

4.5 Organic Acids

Organic acids that may be used in the disclosed compositions include lactic acid, citric acid, salicylic acid, glycolic acid, mandelic acid, benzoic acid and combinations thereof. In non-limiting examples, an organic acid may be at a concentration between about 0.1 and about 2% w/w.

4.6 Additional Components

The compositions may contain additional components known in the art for use in soaps, skin sanitizers, and other topical compositions.

In certain non-limiting embodiments, the composition may comprise a polyethylene oxide (Polyox) hydrogel polymer which, without being bound to any particular theory, can help the skin retain moisture.

In certain non-limiting embodiments, the composition may comprise an anti-irritant component, for example a zinc salt, such as zinc gluconate, alpha bisabolol, aloe gel/leaf juice, oat beta glucan, oat flour, oat extract and combinations thereof. Further non-limiting examples of zinc salts that may be used include zinc acetate, zinc butyrate, zinc citrate, zinc glycerate, zinc glycolate, zinc formate, zinc lactate, zinc picolinate, zinc propionate, zinc salicylate, zinc tartrate, zinc undecylenate, zinc oxide, zinc stearate and combinations thereof. For example, a combination of aloe gel/leaf juice and alpha bisabolol may be used where the ratio of bisabolol to aloe gel/leaf juice may be between about 1:1 to 1:10. In non-limiting embodiments, the concentration of zinc salt may be between about 0.1 and about 2.0% w/w, the concentration of bisabolol may be between about 0.01 and about 0.2% w/w, and/or the concentration of Aloe gel/leaf juice may be between about 0.125 and about 2.0%. In non-limiting embodiments, the oat beta glucan, the oat flour or oat extract may be between about 0.5-5.0% w/w.

For example, a composition disclosed herein may further comprise a thickening and/or gelling agent such as polyethylene oxide (Polyox) hydrogel polymer, stearyl alcohol, cellulose polymer, cationic hydroxy ethyl cellulose (e.g., Ucare; JR30), hydroxy propyl methyl cellulose, hydroxy propyl cellulose (Klucel), chitosan pyrrolidone carboxylate (Kytamer), behenyl alcohol, zinc stearate, emulsifying waxes, including but not limited to Incroquat and Polawax, an addition polymer of acrylic acid, a resin such as Carbopol® ETD 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, isocetyl alcohol, isostearyl alcohol, karaya gum, kelp, lauryl alcohol, locust bean gum, magnesium aluminium silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminium polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacrylate, sodium silicoaluminate, sodium sulfate, stearalkonium bentotnite, stearalkonium hectorite, stearyl alcohol, tallow alcohol, TEA-hydrochloride, tragacanth gum, tridecyl alcohol, tromethamine magnesium aluminium silicate, wheat flour, wheat starch, xanthan gum, abietyl alcohol, acrylinoleic acid, aluminum behenate, aluminum caprylate, aluminum dilinoleate, aluminum salts, such as distearate, and aluminum isostearates, beeswax, behenamide, butadiene/acrylonitrile copolymer, C29-70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl triacetyl hydroxystearate, glyceryl tri-acetyl ricinolate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhyrdine copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, ophthalmic anhydride/glycerin/glycidyl decanoate copolymer, ophthalmic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eiconsene copolymer, PVP/hexadecene copolymer, rice bran wax, stearlkonium bentonite, stearalkonium hectorite, stearamide, stearamide DEA-distearate, stearamide DIBA-stearate, stearamide MEA-stearate, stearone, stearyl erucamide, stearyl stearate, stearyl stearoyl stearate, synthetic beeswax, synthetic wax, trihydroxystearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof. Gelling agents used in vehicles may be natural gelling agents such as natural gums, starches, pectins, agar and gelatin, and may be based on polysaccharides or proteins Examples include but are not limited to guar gum, xanthum gum, alginic acid (E400), sodium alginate (E401), potassium alginate (E402), ammonium alginate (E403), calcium alginate (E404,—polysaccharides from brown algae), agar (E406, a polysaccharide obtained from red seaweeds), carrageenan (E407, a polysaccharide obtained from red seaweeds), locust bean gum (E410, a natural gum from the seeds of the Carob tree), pectin (E440, a polysaccharide obtained from apple or citrus-fruit), and gelatin (E441, made by partial hydrolysis of animal collagen), pentylene glycol 4-t-nutylcyclohexanol (Symsitive 1609).

A composition as disclosed herein may optionally further comprise a surfactant. The surfactant may be a cationic surfactant, an ampholytic surfactant, or a nonionic surfactant. Non-limiting examples of surfactants include polyethoxylates, fatty alcohols (e.g., ceteth-20 (a cetyl ether of polyethylene oxide having an average of about 20 ethylene oxide units) and other "BRIJ"™ nonionic surfactants available from ICI Americas, Inc. (Wilmington, Del.)), cocamidopropyl betaine, alkyl phenols, fatty acid esters of sorbitol, sorbitan, or polyoxyethylene sorbitan.

A composition as disclosed herein may optionally further comprise an alcohol or a mixture of alcohols, for example, ethanol, isopropyl alcohol, n-propyl alcohol, and mixtures thereof; fatty alcohols, including, but not limited to, cetyl alcohol, myristol alcohol, stearyl alcohol, octyl alcohol, decyl alcohol and lauryl alcohol, and mixtures thereof; hexanol, and/or other aliphatic or aromatic alcohol.

A composition as disclosed herein may optionally further comprise a silicone polymer or silicone fluid, for example one or more than one polydimethylsiloxane polymer (Dow Coning 225 Silicone Fluid), dimethiconol fluid in dimethicone (Dow Corning 1403 Silicone Fluid), Silsurf J208

(Siltech LLC, 30019) cyclomethicone and dimethicone copolyl (Dow Corning 3225C Silicone Fluid), Dow Corning 190 and 193 surfactants, polyarylsiloxanes, polyalkylarylsiloxanes, polysiloxane gums, polyether siloxane copolymers, dimethicone polysiloxane, dimethiconol, polysiloxanes, polysiloxane copolymers, polyalkyl aryl silanes, polyaryl siloxanes, polyalkyl siloxanes, polyalkyl aryl silanes, polysiloxane copolymers, alkyl dimethicones, alkylmethicones, alkyldimethicone copoloyls, phenyl silicones, alkyl trimethylsilanes, dimethicone crosspolymer, trisiloxaDC silicone fluid 1404, 1503, silicone glycol (BASF 1066 DCG polyol), GE silicones, dimethicones, cyclomethicones, Bis PEG 15 Methyl ether dimethicone, Dow Corning 2501 cosmetic wax, and combinations thereof.

A composition as disclosed herein may optionally further comprise one or more essential oil and/or individual constituent thereof, one or more additives such as dyes, fragrances, pH adjusters, including basic pH adjusters such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine); acid pH adjusters such as mineral acids and polycarboxylic acids; vitamins such as vitamin A, vitamin E and vitamin C; polyamino acids and salts, such as ethylenediamine tetraacidic acid (EDTA), preservatives such as Germall plus and DMDM hydantoin, and sunscreens such as aminobenzoic acid, arobenzone, cinoxate, diioxybenzone, homosalate, menthyl anthranilate, octocrylene, octyl methoxycinnamate, octyl salicylate, oxybenzoate, padimate 0, phenylbenzimidazole, sulfonic acid, sulisobenzone, titanium dioxide, trolamine salicylate and zinc oxide.

In certain non-limiting embodiments the composition does not contain a cationic emulsifier selected from the group consisting of include incroquat compounds such as (but not limited to) behenyltrimonium methosulfate in cetearyl alcohol (e.g., incroquat behenyl TMS and incroquat behenyl TMS 50 (Croda Inc., Edison, N.J.)), behenalkonium chloride and cetyl alcohol (e.g., Incroquat B-65 (Croda Inc., Edison, N.J.)), behenamido propyl ethyl dimonium ethosulfate and stearyl alcohol (Incroquat BES-35 S (Croda Inc., Edison, N.J.)), steralkonium chloride and cetearyl alcohol and PEG-40 Castor oil (e.g., Incroquat CR concentrate (Croda Inc., Edison, N.J.)), Incroquat CTC-30 (Croda Inc., Edison, N.J.), Incroquat DBM-90 (Croda Inc., Edison, N.J.), Incroquat 0-50 (Croda Inc., Edison, N.J.), Incroquat S-DQ-25 (Croda Inc., Edison, N.J.), Incroquat BA-85 (Croda Inc., Edison, N.J.), Incroquat WG-85 (Croda Inc., Edison, N.J.), as well as distearyldimonium chloride (e.g., VARISOFT® TA 100 (Essen-Degussa, Germany)), palmitamidopropyltrimonium chloride (e.g., VARISOFT® PATC (Essen-Degussa, Germany)), and cetearyl alcohol (and) palmitamidopropyltrimonium chloride (e.g., TEGO® Care CE 40).

4.7 Compositions/Methods of Use

In non-limiting embodiments, the compositions are embodied as soap, cleansing foam, leave-on hand sanitizer, alcohol-containing hand sanitizer or soap, alcohol-free hand sanitizer or soap, lotion, cream, splash, astringent, or wipe formulations. The formulations may be applied to humans or non-human animals (for example, for veterinary or agricultural purposes). Non-limiting examples are described below by way of illustration but further embodiments would be envisaged by the person of skill in the art.

In one set of non-limiting embodiments, the composition is a soap comprising the following components:

| Ingredients | (% w/w) |
|---|---|
| Benzyl alcohol | 1.0-3.0 |
| Benzethonium chloride and/or Benzalkonium chloride | 0.1-0.23 |
| Biguanide | 0.05-0.6 |
| Dipropylene Glycol and/or diglycerin | 1.0-5.0 |
| Farnesol | 0.3-3.0 |
| Organic acid | 0.0-2.0 |

This composition may further contain one or more of the following anti-irritants:

| | |
|---|---|
| Zinc gluconate/Zinc lactate | 0.1-0.2 |
| Bisabolol | 0.01-0.2 |
| *Aloe* leaf juice | 0.125-1.0 |

This composition may have a pH between about 5 and about 6.8.

In one specific non-limiting embodiment, the composition is a soap having the following formulation:

| Ingredients | (% w/w) |
|---|---|
| Benzyl alcohol | 1.0-3.0 |
| Benzethonium chloride/Benzalkonium chloride | 0.1-0.23 |
| Chlorhexidine and/or PHMB | 0.05-0.6 |
| Dipropylene Glycol/diglycerin | 1.0-5.0 |
| Farnesol | 0.3-3.0 |
| Organic acid | 0.0-2.0 |
| Pluronic F-87 prill | 0.5-2.0 |
| Hydroxypropyl methylcellulose (Methocel) | 0.1-0.5 |
| Non ionic poly (ethylene Oxide) Polymer (Polyox) | 0.1-1.0 |
| Incromine Oxide L | 3.0-5.0 |
| Montalene C 40 | 3.0-8.0 |
| Germall Plus | 0.0-2.0 |
| Water | 55-70 |
| Glycerin | 1.0-3.0 |
| SDA-40 B alcohol | 5.0-15 |
| Butylene glycol | 1.0-3.0 |
| Dehydroquat (Cetrimonium chloride) | 0-2.0 |
| Phenoxyethanol/Phenylethanol | 0.0-1.0 |
| Alkanediol | 0.2-2.0 |
| Zinc gluconate/Zinc lactate | 0-0.2 |
| Bisabolol | 0-0.2 |
| *Aloe* leaf juice | 0-1.0 |

This composition may have a pH between about 5 and about 6.8.

In one specific non-limiting embodiment, the composition is a soap ("LPS-14E") having the following formulation:

| Ingredients | % w/w |
|---|---|
| Benzyl alcohol | 2.0 |
| Benzethonium chloride | 0.23 |
| Dipropylene Glycol | 5.0 |
| Farnesol | 1.0 |
| Lactic acid | 0.2 |
| Zinc gluconate | 0.2 |
| Pluronic F-87 prill | 1.0 |
| Methocel E4 M | 0.2 |
| PolyoxWSR 205 | 0.3 |
| Incromine Oxide L | 5.0 |
| Montalene C 40 | 8.0 |
| Germall Plus | 0.2 |
| Water | 64.27 |
| Glycerine | 1.0 |
| SDA-40 B alcohol | 8.0 |

| Ingredients | % w/w |
| --- | --- |
| Butylene glycol | 1.0 |
| Phenoxyethanol | 1.0 |
| PHMB | 0.4 |
| Octanediol | 1.0 |
| pH 5.2-5.5 | |

In one specific non-limiting embodiment, the composition is a soap ("LPS-14F") having the following formulation:

| Ingredients | % w/w |
| --- | --- |
| Benzyl alcohol | 2.0 |
| Benzethonium chloride | 0.23 |
| PHMB | 0.4 |
| Dipropylene Glycol | 5.0 |
| Farnesol | 2.0 |
| Zinc gluconate | 0.2 |
| Pluronic F-87 prill | 1.0 |
| Methocel E4 M | 0.2 |
| PolyoxWSR 205 | 0.5 |
| Incromine Oxide L | 3.0 |
| Montalene C 40 | 8.0 |
| Water | 57.12 |
| Glycerine | 1.0 |
| SDA-40 B alcohol | 15.0 |
| Butylene glycol | 1.0 |
| Phenoxyethanol | 1.0 |
| Octanediol | 1.0 |
| Dehydroquat | 1.0 |
| Bisabolol | 0.025 |
| *Aloe* leaf juice | 0.25 |
| pH 5.2-5.5 | |

In one specific non-limiting embodiment, the composition is a soap ("LPS-14F7-2") having the following formulation:

| Ingredients | % w/w |
| --- | --- |
| Benzyl alcohol | 2.0 |
| Benzethonium chloride | 0.23 |
| PHMB | 0.4 |
| Dipropylene Glycol | 5.0 |
| Farnesol | 2.0 |
| Zinc gluconate | 0.2 |
| Bisabolol | 0.1 |
| *Aloe* leaf juice | 0.25 |
| Pluronic F-87 prill | 1.0 |
| Methocel E4 M | 0.2 |
| PolyoxWSR 205 | 0.3 |
| Incromine Oxide L | 3.42 |
| Montalene C 40 | 8.0 |
| Water | 57.3 |
| Glycerin | 1.0 |
| SDA-40 B alcohol | 14.0 |
| Butylene glycol | 1.0 |
| Phenoxyethanol | 1.0 |
| Octanediol | 1.0 |
| pH 5.6-6.0 | |

In one specific non-limiting embodiment, the composition is a soap having the following formulation:

| Ingredients | (% w/w) |
| --- | --- |
| Pluronic F-87 prill | 0.5-1.0 |
| Methocel E4 M | 0.1-0.5 |
| PolyoxWSR 205 | 0.1-0.5 |
| Incromine Oxide L | 3.0-5.0 |
| Montalene C 40 | 3.0-8.0 |
| Germall Plus | 0.0-2.0 |
| Water | 55-70 |
| Zinc gluconate | 0.0-0.2 |
| Glycerin | 1.0-3.0 |
| SDA-40 B alcohol | 5.0-15 |
| Butylene glycol | 1.0-3.0 |
| Benzyl alcohol | 1.0-3.0 |
| Fruit acid | 0.1-2.0 |
| Benzethonium chloride and/or Benzalkonium chloride | 0.1-0.23 |
| Dipropylene Glycol and/or diglycerin | 1.0-5.0 |
| Farnesol | 0.3-2.0 |
| Phenoxyethanol and/or Phenylthanol | 0.0-1.0 |
| Chlorhexidine and/or PHMB | 0.05-0.6 |
| Alkanediol | 0.2-2.0 |

In one specific non-limiting embodiment, the composition is a soap having the following formulation:

| Ingredients | (% w/w) |
| --- | --- |
| Pluronic F-87 prill | 0.5-1.0 |
| Methocel E4 M | 0.1-0.5 |
| PolyoxWSR 205 | 0.1-0.5 |
| Incromine Oxide L | 3.0-5.0 |
| Montalene C 40 | 3.0-8.0 |
| Water | 50-70 |
| Zinc gluconate | 0.1-0.2 |
| Glycerine | 1.0-3.0 |
| SDA-40 B alcohol | 5.0-15 |
| Butylene glycol | 1.0-3.0 |
| Benzyl alcohol | 1.0-3.0 |
| Benzethonium chloride | 0.1-0.23 |
| Dipropylene Glycol | 1.0-5.0 |
| Farnesol | 0.3-3.0 |
| Phenoxyethanol | 0.0-1.0 |
| PHMB | 0.05-0.6 |
| Octanediol | 0.2-2.0 |
| Bisabolol | 0.01-1.0 |
| *Aloe* leaf juice | 0.1-2.0 |

In one specific non-limiting embodiment, the composition is a soap ("LPS 3") having the following formulation:

| Ingredients | (% w/w) |
| --- | --- |
| Pluronic F-87 prill | 1.00 |
| Methocel E4 M | 0.2 |
| PolyoxWSR 205 | 0.3 |
| Incromine Oxide L | 3.42 |
| Montalene C 40 | 8.0 |
| Water | 57.3 |
| Zinc gluconate | 0.2 |
| Glycerine | 1.0 |
| SDA-40 B alcohol | 14.0 |
| Butylene glycol | 1.0 |
| Benzyl alcohol | 2.0 |
| Benzethonium chloride | 0.23 |
| Dipropylene Glycol | 5.0 |
| Farnesol | 2.0 |
| Phenoxyethanol | 1.0 |
| PHMB | 0.4 |
| Octanediol | 1.0 |
| Bisabolol | 0.1 |
| *Aloe* leaf juice | 0.25 |

In one specific non-limiting embodiment, the composition is a soap having the following formulation:

| Ingredients | (% w/w) |
| --- | --- |
| Benzyl alcohol | 2.0 |
| Benzethonium chloride | 0.23 |
| PHMB | 0.4 |
| Dipropylene Glycol | 5.0 |
| Farnesol | 2.0 |
| Zinc gluconate | 0.2 |
| Bisabolol | 0.1 |
| *Aloe* leaf juice | 0.25 |
| Pluronic F-87 prill | 1.0 |
| Methocel E4 M | 0.2 |
| PolyoxWSR 205 | 0.3 |
| Incromine Oxide L | 3.42 |
| Montalene C 40 | 8.0 |
| Water | 57.3 |
| Glycerine | 1.0 |
| SDA-40 B alcohol | 14.0 |
| Butylene glycol | 1.0 |
| Phenoxyethanol | 1.0 |
| Octanediol | 1.0 |

In one specific non-limiting embodiment, the composition is a soap having the following formulation:

| Ingredients | (% w/w) |
| --- | --- |
| Benzyl alcohol | 2.0 |
| Benzethonium chloride | 0.23 |
| PHMB | 0.4 |
| Dipropylene Glycol | 5.0 |
| Zinc gluconate | 0.2 |
| Bisabolol | 0.1 |
| *Aloe* leaf juice | 0.25 |
| Pluronic F-87 prill | 1.0 |
| Methocel E4 M | 0.2 |
| PolyoxWSR 205 | 0.3 |
| Incromine Oxide L | 3.42 |
| Montalene C 40 | 8.0 |
| Water | 59.3 |
| Glycerine | 1.0 |
| SDA-40 B alcohol | 14.0 |
| Butylene glycol | 1.0 |
| Phenoxyethanol | 1.0 |
| Octanediol | 1.0 |

In one specific non-limiting embodiment, the composition is a soap having the following formulation:

| Ingredients | (% w/w) |
| --- | --- |
| Benzethonium chloride | 0.23 |
| PHMB | 0.4 |
| Dipropylene Glycol | 5.0 |
| Farnesol | 2.0 |
| Zinc gluconate | 0.2 |
| Bisabolol | 0.1 |
| *Aloe* leaf juice | 0.25 |
| Pluronic F-87 prill | 1.0 |
| Methocel E4 M | 0.2 |
| PolyoxWSR 205 | 0.3 |
| Incromine Oxide L | 3.42 |
| Montalene C 40 | 8.0 |
| Water | 59.3 |
| Glycerine | 1.0 |
| SDA-40 B alcohol | 14.0 |
| Butylene glycol | 1.0 |
| Phenoxyethanol | 1.0 |
| Octanediol | 1.0 |

In one specific non-limiting embodiment, the composition is a soap having the following formulation:

| Ingredients | (% w/w) |
| --- | --- |
| Benzyl alcohol | 2.0 |
| Benzethonium chloride | 0.23 |
| PHMB | 0.4 |
| Dipropylene Glycol | 5.0 |
| Nerolidol | 2.0 |
| Zinc gluconate | 0.2 |
| Bisabolol | 0.1 |
| *Aloe* leaf juice | 0.25 |
| Pluronic F-87 prill | 1.0 |
| Methocel E4 M | 0.2 |
| PolyoxWSR 205 | 0.3 |
| Incromine Oxide L | 3.42 |
| Montalene C 40 | 8.0 |
| Water | 57.3 |
| Glycerine | 1.0 |
| SDA-40 B alcohol | 14.0 |
| Butylene glycol | 1.0 |
| Phenoxyethanol | 1.0 |
| Octanediol | 1.0 |

In one specific non-limiting embodiment, the composition is a soap having the following formulation:

| Ingredients | (% w/w) |
| --- | --- |
| Benzyl alcohol | 2.0 |
| Benzethonium chloride | 0.23 |
| PHMB | 0.4 |
| Dipropylene Glycol | 5.0 |
| Bisabolol | 2.0 |
| Zinc gluconate | 0.2 |
| Bisabolol | 0.1 |
| *Aloe* leaf juice | 0.25 |
| Pluronic F-87 prill | 1.0 |
| Methocel E4 M | 0.2 |
| PolyoxWSR 205 | 0.3 |
| Incromine Oxide L | 3.42 |
| Montalene C 40 | 8.0 |
| Water | 57.3 |
| Glycerine | 1.0 |
| SDA-40 B alcohol | 14.0 |
| Butylene glycol | 1.0 |
| Phenoxyethanol | 1.0 |
| Octanediol | 1.0 |

In one specific non-limiting embodiment, the composition is a soap having the following formulation:

| Ingredients | (% w/w) |
| --- | --- |
| Benzyl alcohol | 2.0 |
| Benzethonium chloride | 0.23 |
| PHMB | 0.4 |
| Dipropylene Glycol | 5.0 |
| Apritone | 2.0 |
| Zinc gluconate | 0.2 |
| Bisabolol | 0.1 |
| *Aloe* leaf juice | 0.25 |
| Pluronic F-87 prill | 1.0 |
| Methocel E4 M | 0.2 |
| Incromine Oxide L | 3.42 |
| Montalene C 40 | 8.0 |
| Water | 57.3 |
| Glycerine | 1.0 |
| SDA-40 B alcohol | 14.0 |
| Butylene glycol | 1.0 |
| Phenoxyethanol | 1.0 |
| Octanediol | 1.0 |

In one set of non-limiting embodiments, the composition is an alcohol-free hand disinfectant foam comprising the following components:

| Ingredients | % w/w |
| --- | --- |
| Benzyl alcohol | 0.5-2.0 |
| Quaternary ammonium compound | 0.1-0.23 |
| PHMB | 0.05-0.6 |
| Dipropylene Glycol | 0.2-5.0 |
| Farnesol | 0.1-0.5 |
| Fruit acid | 0.-2.0 |

The composition may optionally further comprise one or more of the following anti-irritants:

| | |
| --- | --- |
| Zinc gluconate | 0.1-0.5 |
| Bisabolol + gingerextract (Symrelief) | 0.05-0.2 |
| Aloe Barbedensis juice/gel | 0.25-1.0 |
| Siliconefluid/Polymer | 0.25-2.0 |

In one specific non-limiting embodiment, the composition is an alcohol-free hand disinfectant foam (HSBZT) having the following formulation:

| Ingredients | %w/w |
| --- | --- |
| Benzyl alcohol | 0.5-2.0 |
| Benzethonium chloride | 0.1-0.23 |
| PHMB | 0.05-0.6 |
| Dipropylene Glycol | 0.2-5.0 |
| Farnesol | 0.1-0.5 |
| Fruit acid | 0.1-2.0 |
| Zinc gluconate | 0.1-0.5 |
| Bisabolol + gingerextract (Symrelief) | 0.05-0.2 |
| Aloe Barbedensis juice/gel | 0.25-1.0 |
| Water | 60-80 |
| Polyox WSR 205 | 0.05-0.2 |
| Pluronic F-87 | 0.5-1.0 |
| Solubilizer 611674 | 0.5-2.0 |
| (PEG-40 Hydrogenated castor oil, Trideceth-9, water) | |
| Phenoxy ethanol | 0.0-1.0 |
| Octanediol | 0.5-2.0. |
| Pentanediol | 0.5-2.0 |
| Arlasilk Phospholipid PTM | 0.0-0.5 |
| Montalene C-40 | 0.25-1.0 |
| Silsurf J208 | 0.25-2.0 |
| pH to 4.00-4.5 | |

In one set of non-limiting embodiments, the composition is an alcohol-free hand disinfectant foam comprising the following components:

| Ingredients | % w/w |
| --- | --- |
| Benzyl alcohol | 0.5-2.0 |
| Benzalkonium chloride | 0.1-0.23 |
| PHMB | 0.05-0.6 |
| Dipropylene Glycol | 0.2-5.0 |
| Farnesol | 0.1-0.5 |
| Lactic acid | 0.1-2.0 |

The composition may optionally further comprise one or more of the following anti-irritants:

| | |
| --- | --- |
| Zinc gluconate/Zinc lactate | 0.1-0.2 |
| Bisabolol + gingerextract (Symrelief) | 0.05-0.2 |
| Aloe Barbedensis juice/gel | 0.25-1.0 |

In one set of non-limiting embodiments, the composition is an alcohol-free hand disinfectant foam comprising the following components:

| Ingredients | (% w/w) |
| --- | --- |
| Water | 60-85 |
| Zinc gluconate | 0.1-0.2 |
| Pluronic F-87 | 0.5-1.0 |
| Bisabolol + gingerextract (Symrelief) | 0.05-0.2 |
| Aloe Barbedensis juice/gel | 0.25-1.0 |
| Benzethonium chloride | 0.1-0.23 |
| PHMB | 0.05-0.6 |
| Phenoxy ethanol | 0.0-1.0 |
| Pentanediol | 0.5-2.0 |
| Montalene C-40 | 0.5-3.0 |
| Benzyl alcohol | 0.5-2.0 |
| Farnesol | 0.5-2.0 |
| Organic acid | 0.2-0.5 |
| Dipropylene Glycol | 0.2-2.0 |
| Propylene glycol | 0.2-1.0 |
| Glycerin | 0.5-2.0 |
| Ultrapure MFB1-1 | 0.2-2.0 |
| pH to 4.00-4.2 | |

In one specific non-limiting embodiment, the composition is an alcohol-free hand disinfectant foam ("AQ-D14") comprising the following components:

| Ingredients | (% w/w) |
| --- | --- |
| Water | 85.0 |
| Zinc gluconate | 0.2 |
| Pluronic F-87 | 1.0 |
| Bisabolol + gingerextract (Symrelief) | 0.05 |
| Aloe Barbedensis juice/gel | 0.5 |
| Benzethonium chloride | 0.18 |
| PHMB | 1.0 |
| Phenoxy ethanol | 0.5 |
| Pentanediol | 1.0 |
| Montalene C-40 | 2.0 |
| Benzyl alcohol | 1.0 |
| Farnesol | 0.3 |
| Organic acid | 0.2 |
| Dipropylene Glycol | 0.5 |
| Propylene glycol | 0.5 |
| Glycerin | 1.0 |
| Ultrapure MFB1-1 | 1.0 |
| pH to 4.00-4.2 | |

In one specific non-limiting embodiment, the composition is an alcohol hand disinfectant foam comprising the following components:

| Ingredient | (% w/w) |
| --- | --- |
| Water | 25-35 |
| SoftcatPolymerSL-100 | 0.05-0.2 |
| Zinc gluconate | 0.1-0.2 |
| Glycerin | 1.0-5.0 |
| Benzethonium chloride | 0.12-2.3 |
| Lactic acid | 0.1-0.2 |
| Glucam P-20 | 0.2-2.0 |
| SDA 40B alcohol | 55-65 |

-continued

| Ingredient | (% w/w) |
|---|---|
| Benzyl alcohol | 0.5-2.0 |
| Lemongrass oil | 0.01-0.03 |
| Dowcorning silicone fluid 190 | 1.0-4.0 |
| *Aloe* leaf juice | 0.3-1.0 |
| Symrelief | 0.03-0.1 |
| Ultrapure MFB -10 | 1.0-5.0 |
| PHMB | 0.1-0.3 |
| pH 4.5-4.6 | |

In one specific non-limiting embodiment, the composition is an alcohol hand disinfectant foam comprising the following components:

| Ingredient | (% w/w) |
|---|---|
| Water | 28.05 |
| SoftcatPolymerSL-100 | 0.05 |
| Zinc gluconate | 0.2 |
| Glycerin | 1.0 |
| Benzathonium chloride | 0.18 |
| Lactic acid | 0.1 |
| Glucam P-20 | 1.0 |
| SDA 40B alcohol | 60.0 |
| Benzyl alcohol | 1.0 |
| Lemongrass oil | 0.02 |
| Dowcorning silicone fluid 190 | 1.0 |
| *Aloe* leaf juice | 0.5 |
| Symrelief | 0.05 |
| Ultrapure MFB -10 | 1.0 |
| PHMB | 0.3 |
| pH 4.5-4.6 | |

In one specific non-limiting embodiment, the composition is an alcohol-free hand disinfectant lotion (HSBAC) having the following formulation:

| Ingredients | % w/w |
|---|---|
| Benzyl alcohol | 0.5-2.0 |
| Benzalkonium chloride | 0.1-0.23 |
| PHMB | 0.05-0.6 |
| Dipropylene Glycol | 0.2-5.0 |
| Farnesol | 0.1-0.5 |
| Lactic acid | 0.1-2.0 |
| Zinc gluconate/Zinc lactate | 0.1-0.2 |
| Bisabolol + gingerextract (Symrelief) | 0.05-0.2 |
| *Aloe Barbedensis* juice/gel | 0.25-1.0 |
| Polyox WSR 205 | 0.05-0.2 |
| Polowax NF | 0.5-2.0 |
| Incroquat TMS | 0.5-4.0 |
| Stearyl alcohol | 0.5-3.0 |
| Isopropyl myristate | 0.5-2.0 |
| Arlacel 165 | 0.5-1.0 |
| Vit. E acetate | 0.2-0.5 |
| Zinc oxide | 0-3.0 |
| Zn stearate | 0.25-1.0 |
| Glycerine | 1.0-3.0 |
| Water | 60-80.0 |
| Polyquaternium 10 | 0.1-0.30 |
| Butylene glycol | 0.5-3.0 |
| Allantoin | 0.2-0.5 |
| Alkanediol | 0.2-1.0 |
| Silicone fluid | 0.3-1.0 |
| pH to 5.5-6.0 | |

In one specific non-limiting embodiment, the composition is an alcohol-free hand disinfectant lotion having the following formulation:

| Ingredients | (% w/w) |
|---|---|
| Polowax NF | 0.5-2.0 |
| Incroquat TMS | 0.5-4.0 |
| Stearyl alcohol | 0.5-3.0 |
| Isopropyl myristate | 0.5-2.0 |
| Arlacel 165 | 0.5-1.0 |
| Vit. E acetate | 0.02-0.5 |
| Zn oxide | 0.0-2.0 |
| Zn stearate | 0.25-0.50 |
| Glycerin | 1.0-3.0 |
| Dipropyleneglycol | 0.5-2.0 |
| Water | 60-85.0 |
| Polyquaternium 10 | 0.1-0.30 |
| Polyox WSR 205 | 0.05-0.2 |
| Butylene glycol | 0.5-3.0 |
| Dipropylene glycol | 0.2-5.0 |
| Farnesol | 0.5-2.0 |
| Zinc gluconate | 0.0-0.2 |
| Lactic acid | 0.1-2.0 |
| Benzalkonium Chloride | 0.1-0.23 |
| PHMB | 0.05-0.6 |
| Benzyl alcohol | 0.5-2.0 |
| Silicone fluid | 0.3-1.0 |
| *Aloe* leaf Juice | 0.01-2.0 |
| Symrelief | 0.01-1.0 |
| Adjust pH to 5.5-6.0 | |

In one specific non-limiting embodiment, the composition is an alcohol-free hand disinfectant lotion ("Lotion D-10") having the following formulation:

| Ingredients | (% w/w) |
|---|---|
| Polowax NF | 2.0 |
| Incroquat TMS | 4.0 |
| Stearyl alcohol | 1.0 |
| Isopropyl myristate | 1.0 |
| Arlacel 165 | 1.0 |
| Vit. E acetate | 0.1 |
| Zn oxide | 0.25 |
| Zn stearate | 0.5 |
| Glycerin | 2.0 |
| Dipropyleneglycol | 1.0 |
| Water | 80.75 |
| Polyquaternium 10 | 0.15 |
| Polyox WSR 205 | 0.1 |
| Butylene glycol | 1.0 |
| Farnesol | 0.3 |
| Zinc gluconate | 0.2 |
| Lactic acid | 0.2 |
| Benzalkonium Chloride | 0.12 |
| PHMB | 0.3 |
| Benzyl alcohol | 1.0 |
| Silicone fluid | 1.0 |
| *Aloe* leaf Juice | 0.5 |
| Symrelief | 0.05 |
| Adjust pH to 5.5-6.0 | |

In one specific non-limiting embodiment, the composition is a wound-healing cream having the following formulation:

| Ingredients | % w/w | Range (% w/w) |
|---|---|---|
| White Petrolatum* | 5.0 | 4-6 |
| Stearyl Alcohol | 13 | 10-15 |
| Isopropyl Myristate | 4.0 | 3-5 |
| Sorbitan Oleate | 1.6 | 1-2 |
| Polyoxyl 40 Stearate(Myrj 52) | 4.0 | 3-5 |
| Dipropyleneglycol | 1.0 | 0.5-3.0 |

-continued

| Ingredients | % w/w | Range (% w/w) |
| --- | --- | --- |
| Incroquat Behenyl TMS | 1.0 | 0.5-3.0 |
| Zinc Oxide | 0.3 | 0.2-1.0 |
| Polawax N.F | 1.0 | 0.5-2.0 |
| Zinc stearate | 0.3 | 0.2-1.0 |
| Water | 63.85 | 55-70 |
| Germall+ | 0.2 | 0.1-0.3 |
| Ascorbic acid(Vitamin C) | 1.0 | 0.5-2.0 |
| *Calendula* Oil | 0.5 | 0.3-1.-0 |
| Benzyl alcohol | 0.1 | 0.1-0.5 |
| PHMB | 0.15 | 0.1-0.3 |
| Benzoic acid | 0.2 | 0.2-0.5 |
| Sodium Benzoate | 0.2 | 0.2-0.5 |
| Resveratrol/*Echinacea purpuria* extract | 0.5 | 0.3-1.0 |
| Zinc lactate/Zinc gluconate | 0.2 | 0.1-0.5 |
| *Aloe* leaf *Barbadensis* juice/*Aloe* gel | 0.5 | 0.25-1.0 |
| Alpha Bisabolol | 0.1 | 0.05-0.2 |
| Adjust pH to 5.8-6.0 | | |

In one specific non-limiting embodiment, the composition is a wound-healing cream having the following formulation:

| Ingredients | % w/w | Range (% w/w) |
| --- | --- | --- |
| White Petrolatum* | 5.0 | 4-6 |
| Stearyl Alcohol | 13 | 10-15 |
| Isopropyl Myristate | 4.0 | 3-5 |
| Sorbitan Oleate | 1.6 | 1-2 |
| Polyoxyl 40 Stearate(Myrj 52) | 4.0 | 3-5 |
| Dipropyleneglycol | 1.0 | 0.5-3.0 |
| Incroquat Behenyl TMS | 1.0 | 0.5-3.0 |
| Zinc Oxide | 0.3 | 0.2-1.0 |
| Polawax N.F | 1.0 | 0.5-2.0 |
| Zinc stearate | 0.3 | 0.2-1.0 |
| Water | 63.85 | 55-70 |
| Germall+ | 0.2 | 0.1-0.3 |
| Ascorbic acid(Vitamin C) | 1.0 | 0.5-2.0 |
| *Calendula* Oil | 0.5 | 0.3-1.-0 |
| Benzyl alcohol | 0.1 | 0.1-0.5 |
| PHMB | 0.15 | 0.1-0.3 |
| Benzoic acid | 0.2 | 0.2-0.5 |
| Sodium Benzoate | 0.2 | 0.2-0.5 |
| Rosemary oil | 0.1 | 0.1-0.3 |
| Resveratrol/*Echinacea purpuria* extract | 0.5 | 0.3-1.0 |
| Pomogranate oil | 0.5 | 0.3-1.0 |
| Zinc lactate/Zinc gluconate | 0.2 | 0.1-0.5 |
| *Aloe* leaf *Barbadensis* juice/*Aloe* gel | 0.5 | 0.25-1.0 |
| Alpha Bisabolol | 0.1 | 0.05-0.2 |
| Adjust pH to 5.8-6.0 | | |

In one specific non-limiting embodiment, the composition is a wound-healing cream having the following formulation:

| Ingredients | % w/w | Range (% w/w) |
| --- | --- | --- |
| White Petrolatum* | 5.0 | 4-6 |
| Polyox WSR 205 | 0.1 | 0.05-0.3 |
| Stearyl Alcohol | 13 | 10-15 |
| Isopropyl Myristate | 4.0 | 3-5 |
| Sorbitan Oleate | 1.6 | 1-2 |
| Polyoxyl 40 Stearate(Myrj 52) | 4.0 | 3-5 |
| Dipropyleneglycol | 2.0 | 0.5-3.0 |
| Incroquat Behenyl TMS | 1.0 | 0.5-3.0 |
| Zinc Oxide | 0.3 | 0.2-1.0 |
| Polawax N.F | 1.0 | 0.5-2.0 |
| Zinc stearate | 0.3 | 0.2-1.0 |
| Water | 63.85 | 55-70 |
| Germall+ | 0.2 | 0.1-0.3 |
| Ascorbic acid(Vitamin C) | 1.0 | 0.5-2.0 |
| Glucan(Symglucan from Symrise) | 5.0 | 2-10 |
| *Calendula* Oil | 0.5 | 0.3-1.-0 |
| PHMB | 0.15 | 0.1-0.3 |
| Benzyl alcohol | 0.1 | 0.1-0.5 |

-continued

| Ingredients | % w/w | Range (% w/w) |
| --- | --- | --- |
| Benzoic acid | 0.2 | 0.2-0.5 |
| Sodium Benzoate | 0.2 | 0.2-0.5 |
| Resveratrol/*Echinacea purpuria* extract | 0.2 | 0.3-1.0 |
| Zinc lactate/Zinc gluconate | 0.2 | 0.1-0.5 |
| *Aloe* leaf *Barbadensis* juice/*Aloe* gel | 0.5 | 0.25-1.0 |
| Alpha Bisabolol | 0.1 | 0.05-0.2 |
| Adjust pH to 5.8-6.0 | | |

In one specific non-limiting embodiment, the composition is a first aid cream having the following formulation:

| Ingredients | (% w/w) |
| --- | --- |
| Silver carbonate | 0.1-0.3 |
| *Calendula* Oil | 0.3-1.-0 |
| Curcumin | 0.1-2.0 |
| Benzyl alcohol | 0.1-0.5 |
| Farnesol | 0.3-0.5 |
| PHMB | 0.1-0.3 |
| Benzoic acid | 0.2-0.5 |
| Zinc gluconate | 0.1-0.5 |
| Alpha Bisabolol | 0.05-0.2 |
| *Aloe* leaf juice | 0.3-1.0 |
| White Petrolatum | 1.0-10.0 |
| Stearyl Alcohol | 5.0-20.0 |
| Isopropyl Myristate | 1.0-6.0 |
| Sorbitan Oleate | 0.5-5.0 |
| Polyoxyl 40 Stearate (Myrj 52) | 1.0-10.0 |
| Germal+ | 0.05-0.2 |
| Zinc Oxide | 0.2-1.0 |
| Zinc stearate | 0.2-1.0 |
| Water | 55-70 |
| Adjust pH to 5.8-6.0 | |

In one specific non-limiting embodiment, the composition is a first aid cream having the following formulation:

| Ingredients | (% w/w) |
| --- | --- |
| Silver carbonate | 0.2 |
| *Calendula* Oil | 0.5 |
| Curcumin | 0.5 |
| Benzyl alcohol | 0.1 |
| Farnesol | 0.1 |
| PHMB | 0.15 |
| Benzoic acid | 0.2 |
| Zinc gluconate | 0.2 |
| Alpha Bisabolol | 0.1 |
| *Aloe* leaf juice | 0.5 |
| White Petrolatum | 5.0 |
| Stearyl Alcohol | 13 |
| Isopropyl Myristate | 4.0 |
| Sorbitan Oleate | 1.6 |
| Polyoxyl 40 Stearate (Myrj 52) | 4.0 |
| Germal+ | 0.2 |
| Zinc Oxide | 0.3 |
| Zinc stearate | 0.3 |
| Water | 59.95 |
| Adjust pH to 5.8-6.0 | |

In one specific non-limiting embodiment, the composition is a wound-healing cream having the following formulation:

| Ingredient | Range (% w/w) |
| --- | --- |
| Stearyl Alcohol | 5.0-20.0 |
| Isopropyl Myristate | 1.0-6.0 |
| Sorbitan Oleate | 0.2-3.0 |
| Polyoxyl 40 Stearate(Myrj 52) | 1.0-6.0 |
| Dipropyleneglycol | 0.1-4.0 |

-continued

| Ingredient | Range (% w/w) |
|---|---|
| Incroquat Behenyl TMS | 0.1-5.0 |
| Zinc Oxide | 0.01-2.0 |
| Polawax N.F | 0.1-3.0 |
| Zinc stearate | 0.05-2.0 |
| Water | 40.0-90.0 |
| Polyox WSR 205 | 0.01-1.0 |
| Benzyl alcohol | 0.0-2.0 |
| Germall+ | 0.05-2.0 |
| Zinc lactate | 0.01-1.0 |
| Zinc gluconate | 0.01-0.1 |
| Ascorbic acid(Vit. C) | 0.01-2.0 |
| *Calendula* oil | 0.01-1.0 |
| Cosmocil | 0.05-3.0 |
| Tetrahydrocurcuminoid | 0.05-2.0 |
| Rosemary oil | 0.05-2.0 |
| Oat beta glucan (Sym glucan) | 0.05-2.0 |
| Oat flour/Oat extract | 0.5-5.0 |
| Resveratrol/*Echinacea* extract | 0.0-2.0 |
| Pomogranate oil | 0.02-2.0 |
| *Aloe* leaf *Barbadensis* juice/*Aloe* gel | 0.5-5.0 |
| Alpha Bisabolol | 0.01-2.0 |

5. EXAMPLE 1

Comparison of Persistent Activities of Commercial Soaps with LPS 14E- and LPS 14 7-2 (the Compositions of which are Described Above).

Method of Testing Substantive Activity:

Pigskins (3 cm$^2$ mounted on petri dishes) were washed with non antibacterial soap and rinsed under running tap water. 3 pairs for control (Soap base) and 3 pairs for test were used. 0.15 ml soap was added to each piece of the pair and rubbed for 30 seconds and rinsed each piece with 75 ml water. After 1 or 2 hours, the pieces were contaminated with 10 μl of 10$^5$ Cfu/ml bacterial culture. After 15 minutes the pieces were rinsed with 10 ml of drug inactivating fluid (DNF). The fluid was diluted and plated on TSA. After incubation at 37° C., the bacterial counts were enumerated and the 3 soaps were compared 1="DC" (0.46% T) Commercial soap containing 0.46% triclosan 2="TPB", Comercial soap containing 0.15% triclosan, PHMB and Benzathonium chloride without emollients 3=LPS 14E Soap with emollients 4=LPS 14F7-2 Soap with emollients Log reduction is calculated from Control Growth which is 1×10$^3$ to 5×10$^3$ cfu (3-3.5 log 10)

The bacteria tested were, *S. aureus*(ATCC 6538) and *E. coli*(ATCC 11229). The results of these experiments are shown in Table 1.

TABLE 1

| Log10 reduction in colony-forming units, mean ± SD | | |
|---|---|---|
| | S. aureus | E. coli |
| DC (0.46% T) | | |
| 1 hour post wash | 0.58 | 0.5 |
| 2 hour post wash | 0.17 | 0.4 |
| TPB (0.15% T) | | |
| 1 hour post wash | 0.9 | 0.7 |
| 2 hour post wash | 0.7 | 0.7 |

TABLE 1-continued

| Log10 reduction in colony-forming units, mean ± SD | | |
|---|---|---|
| | S. aureus | E. coli |
| LPS 14E | | |
| 1 hour post wash | 1.8 | 1.6 |
| 2 hour post wash | 1.74 | 1.6 |
| LPS 14F7-2 | | |
| 1 hour post wash | 2.3 | 1.8 |
| 2 hour post wash | 1.9 | 1.9 |

Conclusion:

Activity against both *S. aureus* (gram positive) and *E. coli* (gram negative) is seen even 2 hour after rinsing the skin with the LPS 14E and soap containing emollients LPS 14 F7-2 soap without lactic acid provides slightly more substantive activity. Both DC and TPB showed lower antimicrobial activity, and the antimicrobial activity of the DC soap deteriorated over the testing interval.

6. EXAMPLE 2

Comparison of Persistent Activities of Commercial Hand Sanitizers with HSBZT and HSBAC (the Compositions of which are Described Above).

A method analogous to that used to test the soaps (above) was used to test persistent antimicrobial activities of hand sanitizers. The test organism was *S. aureus* and HSP is a commercial alcohol-based hand sanitizer. The results are shown in Table 2.

TABLE 2

| | Log10 reduction from control counts | |
|---|---|---|
| Disinfectant | 1 hour post application | 4 hour Post application |
| HSBZT | 2.851 | 2.130 |
| HSBAC | 3.2 | 2.9 |
| HSP | 0.102 | 0.050 |

Conclusion Both aqueous HSBZT and HSBAC show grater activity than the commercial alcohol-based hand sanitizer tested.

7. EXAMPLE 3

Evaluation of Anti Irritant Composition (ZAB) in an Alcohol Based Hand Disinfectant Alcohol Based Hand Disinfectant (ABHD)

| Ingredients | % w/w |
|---|---|
| Alcohol SDA 40 B | 70.0 |
| Benzyl alcohol | 1.0 |
| Lactic acid | 0.2 |
| Octanediol | 1.0 |
| Dipropylene glycol | 1.0 |
| Farnesol | 0.5 |
| Benzathonium chloride | 0.18 |
| PHMB | 0.3 |
| Polyquaternium -10 | 0.1 |

-continued

| Ingredients | % w/w |
|---|---|
| Hydroxypropyl methyl cellulose | 0.1 |
| Incromine oxide | 1.0 |
| Water | 23.62 |
| Total | 99.0 |

ABHD with the following ingredients were prepared for testing in volunteers for anti irritant effect. These ingredients were added to the above ABHD and total weight adjusted to 100 gm with water

| | |
|---|---|
| ABHD Z | ABHD containing 0.2% zincgluconate |
| ABHDZ1 | ABHD containing 0.2% zincgluconate + 0.2% Zinc lactate |
| ABHD ZA | ABHD containing 0.2% zinc gluconate + 0.5% *Aloe* leaf juice |
| ABHD ZB | ABHD containing 0.2% zinc gluconate + 0.2% bisabolol |
| ABHD ZAB | ABHD containing 0.2% zinc gluconate + 0.5% Aloeleaf Juice + 0.2% bisabolol |
| ABHD ZAB 1 | ABHD containing 0.2% zincgluconate + 0.25% Aloeleaf Juice + 0.1% bisabolol |

Volunteer Test Results:

Volunteer A had severe irritation when ABHD was applied on the hand.

Volunteer B had moderate reaction

These two volunteers were used for the test.

Test Method:

2 ml of the product is applied on the hand and dried the reaction was observed after 10 minutes The hands were washed and dried After 1 hour the second product was applied. Thus each product was applied after 1 hour interval between application.

Grading of Irritation

0=No reaction

1=Mild itching

2=Moderate itching

3=Severe itching/slight redness

The results are shown in Table 3.

TABLE 3

| | Reaction | |
|---|---|---|
| Group | Volunteer A | Volunteer B |
| ABHD | 3.0 | 2.0 |
| ABHD Z | 3.0 | 2.0 |
| ABHDZ1 | 2.5 | 1.5 |
| ABHD ZA | 1.5 | 0 |
| ABHD ZB | 2.0 | 0.5 |
| ABHD ZAB | 0 | 0 |
| ABHD ZAB 1 | 1.0 | 0 |

Conclusion: ZAB provides good anti irritant protection. The alcohol based hand disinfectant (ABHD produced ABHD) without anti irritant Zinc salts produced severe itching and some redness (grading #3).

8. EXAMPLE 4

Evaluation of Emollients in Hand Disinfectant Antimicrobial Compositions

TABLE 4

Formulations containing various emollients

| | % w/w | | |
|---|---|---|---|
| Ingredients | A | B | C |
| Benzyl alcohol | 2.0 | 2.0 | — |
| Benzethonium chloride | 0.23 | 0.23 | 0.23 |
| PHMB | 0.4 | 0.4 | 0.4 |
| Dipropylene Glycol | 5.0 | 5.0 | 5.0 |
| Farnesol | 2.0 | — | 2.0 |
| Zinc gluconate | 0.2 | 0.2 | 0.2 |
| Bisabolol | 0.1 | 0.1 | 0.1 |
| *Aloe* leaf juice | 0.25 | 0.25 | 0.25 |
| Pluronic F-87 prill | 1.0 | 1.0 | 1.0 |
| Methocel E4 M | 0.2 | 0.2 | 0.2 |
| PolyoxWSR 205 | 0.3 | 0.3 | 0.3 |
| Incromine Oxide L | 3.42 | 3.42 | 3.42 |
| Montalene C 40 | 8.0 | 8.0 | 8.0 |
| Water | 57.3 | 59.3 | 59.3 |
| Glycerine | 1.0 | 1.0 | 1.0 |
| SDA-40 B alcohol | 14.0 | 14.0 | 14.0 |
| Butylene glycol | 1.0 | 1.0 | 1.0 |
| Phenoxyethanol | 1.0 | 1.0 | 1.0 |
| Octanediol | 1.0 | 1.0 | 1.0 |

Composition (A) was formulated with both benzyl alcohol and farnesol; composition (B) was formulated with benzyl alcohol without farnesol; and composition (C) was formulated with farnesol without benzyl alcohol.

Method of Testing Substantive Activity

Pigskins (3 cm$^2$ mounted on petri dishes) were washed with non antibacterial soap and rinsed under running tap water. 3 pairs for control (Soap base) and 3 pairs for testing were used. 0.15 ml soap was added to each piece of the pair and rubbed for 30 seconds and each piece was rinsed with 75 ml water. After 1 or 2 hours, the pieces were contaminated with 10 µl of 10$^5$ Cfu/ml bacterial culture. After 15 minutes the pieces were rinsed with 10 ml of drug inactivating fluid (DNF). The fluid was diluted and plated on TSA. After incubation at 37° C., the bacterial counts were enumerated and the soap compositions were compared. The results are shown in Table 5.

TABLE 5

Substantive antibacterial activity after one time application of soap by pig skin method against, *E. coli* (ATCC 11229)

| SOAP | Log$_{10}$ reduction in colony-forming units from control growth |
|---|---|
| A | 1.8 |
| B | 1.0 |
| C | 0.7 |

Conclusion: From the above results it is concluded that farnesol and benzyl alcohol provide substantive antibacterial efficacy. Dipropylene glycol acts to dissolve farnesol.

The effect of different sesquiterpenoids on substantive antibacterial activity was also examined using the methods described above. The sesquiterpenoids nerolidol, bisabolol and apritone were examined using the formulations described below in Table 6.

TABLE 6

| Ingredients | % w/w | | | |
|---|---|---|---|---|
| | A | B | C | D |
| Benzyl alcohol | 2.0 | 2.0 | 2.0 | 2.0 |
| Benzethonium chloride | 0.23 | 0.23 | 0.23 | 0.23 |
| PHMB | 0.4 | 0.4 | 0.4 | 0.4 |
| Dipropylene Glycol | 5.0 | 5.0 | 5.0 | 5.0 |
| Farnesol | 2.0 | — | — | — |
| Nerolidol | — | 2.0 | — | — |
| Bisabolol | — | — | 2.0 | — |
| Apritone | — | — | — | 2.0 |
| Zinc gluconate | 0.2 | 0.2 | 0.2 | 0.2 |
| Bisabolol | 0.1 | 0.1 | 0.1 | 0.1 |
| *Aloe* leaf juice | 0.25 | 0.25 | 0.25 | 0.25 |
| Pluronic F-87 prill | 1.0 | 1.0 | 3.0 | 1.0 |
| Methocel E4 M | 0.2 | 0.2 | 0.2 | 0.2 |
| PolyoxWSR 205 | 0.3 | 0.3 | 0.3 | — |
| Incromine Oxide L | 3.42 | 3.42 | 3.42 | 3.42 |
| Montalene C 40 | 8.0 | 8.0 | 8.0 | 8.0 |
| Water | 57.3 | 57.3 | 57.3 | 57.3 |
| Glycerine | 1.0 | 1.0 | 1.0 | 1.0 |
| SDA-40 B alcohol | 14.0 | 14.0 | 14.0 | 14.0 |
| Butylene glycol | 1.0 | 1.0 | 1.0 | 1.0 |
| Phenoxyethanol | 1.0 | 1.0 | 1.0 | 1.0 |
| Octanediol | 1.0 | 1.0 | 1.0 | 1.0 |

The antibacterial effects of the compositions described in Table 6 were tested using the pigskin assay method described above. The results are shown below in Table 7.

TABLE 7

Substantive antibacterial activity with various sesquiterpenoids against *E. coli* (ATCC 11229)

| SOAP | $Log_{10}$ reduction in colony-forming units, mean ± SD |
|---|---|
| A | |
| 1 hour post wash | 1.8 |
| B | |
| 1 hour post wash | 1.5 |
| C | |
| 1 hour post wash | 1.6 |
| D | |
| 1 hour post wash | 1.7 |

Conclusion: All the sesquiterpenoids tested have similar substantive antibacterial efficacy.

9. EXAMPLE 5

Evaluation of Substantive Activity and Test Results of an Antibacterial Soap Formulation (LPS 3, Described Above)

Method of Testing Substantive Activity

Pigskins (3 cm² mounted on petri dishes) were washed with non antibacterial soap and rinsed under running tap water. 3 pairs for control (Soap base) and 3 pairs for testing were used. 0.15 ml soap was added to each piece of the pair and rubbed for 30 seconds and each piece was rinsed with 75 ml water. After 1 or 2 Hour, the pieces were contaminated with 10 µl of $10^5$ Cfu/ml bacterial culture. After 15 minutes the pieces were rinsed with 10 ml of drug inactivating fluid (DNF). The fluid was diluted and plated on TSA. After incubation at 37° C., the bacterial counts were enumerated and the effect of the three soaps were compared.

The following formulations were tested:
1 DC (0.46% T): Commercial soap containing 0.46% triclosan (T) (Dial).
2 TPB (0.15% T): Soap containing 0.15% triclosan (T), PHMB and benzethonium chloride without emollients.
3 LPS 3 Soap with emollients.
The results are described in Table 8.

TABLE 8

Antibacterial activity after a single one time application of soap against *S. aureus* (ATCC 6538) and *E. coli* (ATCC 11229)

| | $Log_{10}$ reduction in colony-forming units, mean ± SD Pigskin Method | |
|---|---|---|
| SOAP | *S. aureus* | *E. coli* |
| DC (0.46% T) | | |
| 1 hour post wash | 0.58 ± 0.208 | 0.5 ± 0.12 |
| 2 hour post wash | 0.17 ± 0.051 | 0.4 ± 0.10 |
| TPB (0.15% T) | | |
| 1 hour post wash | 0.9 ± 0.21 | 0.7 ± 0.11 |
| 2 hour post wash | 0.7 ± 0.18 | 0.7 ± 0.20 |
| LPS -3 | | |
| 1 hour post wash | 2.3 ± 0.26 | 1.8 ± 0.21 |
| 2 hour post wash | 1.94 ± 0.27 | 1.9 ± 0.10 |

Control growth ranged from $1 \times 10^3$ to $5 \times 10^3$ cfu

Conclusion: Activity against both *S. aureus* (Gram positive) and *E. coli* (Gram negative) bacteria was seen even 2 hours after rinsing skin that had been treated with the LPS 3 soap containing emollients. The TPB soap, which contains antibacterial agents but no emollients, did not exhibit any substantive antibacterial activity against *S. aureus* and *E. coli*. Dial soap, which contains a higher concentration of triclosan, also showed no significant substantive antibacterial activity in this assay against *S. aureus* and *E. coli*.

The antibacterial efficacy of alcohol-free hand sanitizer formulations was also examined using the methods described above.

TABLE 9

Comparison of the substantive antibacterial efficacy of alcohol-free hand sanitizers by pigskin method-C (Test organism *S. aureus*)

| | $Log_{10}$ reduction from control counts | |
|---|---|---|
| Disinfectant | 1 hour post application | 2 hour Post application |
| AQ-D14 | 2.851 | 2.130 |
| Lotion D-10 | 3.2 | 2.9 |
| HSP | 0.102 | 0.050 |

HSP: alcohol based hand sanitizer Purell

Conclusion: Both of the AQ-D14 and Lotion D-10 alcohol-free hand sanitizers show greater activity than the commercial alcohol-based hand sanitizer tested.

Various patent and non-patent references are cited herein, the contents of which are hereby incorporated by reference in their entireties herein.

We claim:
1. A method comprising:
 applying to a skin surface a topical antimicrobial composition comprising:
 (a) about 0.1-3.0% w/w benzyl alcohol;
 (b) about 0.05-1.0% w/w chlorhexidine salt;
 (c) about 0.3-3.0% w/w farnesol;

(d) about 1.0-5.0% w/w emollient solvents selected from the group consisting of glycerin, ethylhexylglycerin and Phenoxyethanol;
(e) about 0.1-1.0% w/w Hydroxypropyl Methyl cellulose;
(f) about 0.1-1.0% w/w organic acid selected from the group consisting of citric acid, lactic acid, benzoic acid and combinations thereof; and
(g) about 15-70% alcohol, with the proviso that the composition does not contain an essential oil;

wherein the composition provides to the skin surface a persistent antimicrobial activity that causes more than a 2 log reduction of bacterial growth from control level when the skin surface is challenged with bacteria at least one hour following the topical application.

2. The method of claim 1, wherein the composition further comprises 0.1-0.4% w/w zinc gluconate.

3. The method of claim 1, wherein the composition further comprises aloe gel, bisabolol or combinations thereof.

4. The method of claim 2, wherein the composition further comprises aloe gel, bisabolol or combinations thereof.

5. The method of claim 1, wherein the composition is selected from the group consisting of a soap, a hand sanitizer, a cream, a lotion, a splash, an astringent and a wipe.

6. The method of claim 2, wherein the composition is selected from the group consisting of a soap, a hand sanitizer, a cream, a lotion, a splash, an astringent and a wipe.

7. The method of claim 3, wherein the composition is selected from the group consisting of a soap, a hand sanitizer, a cream, a lotion, a splash, an astringent and a wipe.

8. The method of claim 4, wherein the composition is selected from the group consisting of a soap, a hand sanitizer, a cream, a lotion, a splash, an astringent and a wipe.

9. A method comprising:
applying to a skin surface a topical antimicrobial composition consisting of:
(a) about 0.1-3.0% w/w benzyl alcohol;
(b) about 0.05-1.0% w/w chlorhexidine salt;
(c) about 0.3-3.0% w/w farnesol;
(d) about 1.0-5.0% w/w emollient solvents selected from the group consisting of glycerin, ethylhexylglycerin and Phenoxyethanol;
(e) about 0.1-1.0% w/w Hydroxypropyl Methyl cellulose;
(f) about 0.1-1.0% w/w organic acid selected from the group consisting of citric acid, lactic acid, benzoic acid and combinations thereof; and
(g) about 15-70% alcohol, wherein the composition provides to the skin surface a persistent antimicrobial activity that causes more than a 2 log reduction of bacterial growth from a control level when the skin surface is challenged with bacteria at least one hour following the topical application.

* * * * *